(12) United States Patent
Almirante et al.

(10) Patent No.: US 9,598,349 B2
(45) Date of Patent: Mar. 21, 2017

(54) QUINONE BASED NITRIC OXIDE DONATING COMPOUNDS FOR OPHTHALMIC USE

(71) Applicant: NICOX SCIENCE IRELAND, Dublin (IE)

(72) Inventors: Nicoletta Almirante, Milan (IT); Laura Storoni, Cesano Maderno (IT); Gael Ronsin, Milan (IT); Elena Bastia, Milan (IT)

(73) Assignee: Nicox Science Ireland, Dublin (IE)

( * ) Notice: Subject to any disclaimer, the term of this patent is extended or adjusted under 35 U.S.C. 154(b) by 0 days.

(21) Appl. No.: 14/784,914

(22) PCT Filed: Apr. 14, 2014

(86) PCT No.: PCT/EP2014/057515
§ 371 (c)(1),
(2) Date: Oct. 15, 2015

(87) PCT Pub. No.: WO2014/170264
PCT Pub. Date: Oct. 23, 2014

(65) Prior Publication Data
US 2016/0145192 A1     May 26, 2016

(30) Foreign Application Priority Data
Apr. 18, 2013 (EP) .................... 13164236

(51) Int. Cl.
*A61K 31/215* (2006.01)
*A61K 31/216* (2006.01)
*A61K 45/06* (2006.01)
*A61K 9/00* (2006.01)
*C07C 203/00* (2006.01)
*C07C 203/04* (2006.01)

(52) U.S. Cl.
CPC .......... *C07C 203/04* (2013.01); *A61K 9/0048* (2013.01); *A61K 31/215* (2013.01); *A61K 31/216* (2013.01); *A61K 45/06* (2013.01); *C07C 203/00* (2013.01); *C07C 2101/16* (2013.01); *C07C 2102/10* (2013.01)

(58) Field of Classification Search
CPC .... A61K 31/215; A61K 31/216; A61K 45/06; A61K 19/0048; C07C 203/00; C07C 203/04; C07C 2101/16; C07C 2102/10
See application file for complete search history.

(56) References Cited

U.S. PATENT DOCUMENTS

2010/0249189 A1    9/2010   Almirante et al.

FOREIGN PATENT DOCUMENTS

EP    0 232 089 A2    8/1987

OTHER PUBLICATIONS

Boschi et la., "NO-Donor Phenols: A New Class of Products Endowed with Antioxidant and Vasodilator Properties," Journal of Medicinal Chemistry, May 1, 2006, pp. 2886-2897, vol. 49, No. 10.
International Search Report of PCT/EP2014/057515 dated Aug. 12, 2014.

*Primary Examiner* — Paul A Zucker
*Assistant Examiner* — Mark Luderer
(74) *Attorney, Agent, or Firm* — Arent Fox LLP

(57) ABSTRACT

The present invention relates to nitric oxide donor compounds having a quinone based structure, to processes for their preparation and to their use in the treatment and/or prophylaxis of glaucoma and ocular hypertension.

25 Claims, No Drawings

QUINONE BASED NITRIC OXIDE DONATING COMPOUNDS FOR OPHTHALMIC USE

CROSS-REFERENCE TO RELATED APPLICATIONS

This application is a National Stage entry of International Application No. PCT/EP2014/057515, filed Apr. 14, 2014, which claims priority to European Patent Application No. 13164236.5, filed Apr. 18, 2013. The disclosures of the prior applications are hereby incorporated in their entirety by reference.

The present invention relates to nitric oxide donor compounds of formula (I) and their use in the treatment and/or prophylaxis of glaucoma and ocular hypertension.

The present invention also relates to combinations comprising nitric oxide donor compounds of formula (I) and one or more further active ingredients for the use in the treatment and/or prophylaxis of glaucoma and ocular hypertension.

Glaucoma, including normotensive and hypertensive glaucoma, is a disease of the eye characterized by a progressive loss of visual field due to irreversible damage to the optic nerve to the point where, if untreated, may result in total blindness. Hypertensive glaucoma occurs when an imbalance in production and drainage of fluid in the eye (aqueous humor) increases eye pressure to unhealthy levels.

Conversely, normotensive glaucoma occurs despite the intraocular pressure is kept to reasonably low levels.

The loss of visual field, in one form of primary open angle glaucoma (POAG), is associated with a sustained increase in the intraocular pressure of the diseased eye. Moreover, elevated intraocular pressure without visual field loss is thought to be indicative of the early stages of this form of POAG.

Normotensive glaucoma is a chronic progressive optic neuropathy resulting in typical optic nerve head changes, retinal nerve fibers layer defects, and characteristic visual field defects. In addition, the chamber angle is open and IOP values within statistical normal limits (lower than 22 mmHg) (Lee et al. 1998; for review, see Hoyng and Kitazawa 2002).

There is evidence that treatment of normotensive glaucoma by lowering IOP can slow the glaucomatous process. A reduction of at least 30% in IOP is needed to induce a favorable alteration in this disease.

Apart from both these main kinds of glaucoma other pathologies can lead to an elevation of IOP, namely secondary glaucoma including post-uveitic glaucoma and steroid-induced glaucoma.

Prior art treatment of glaucoma consists in lowering the intraocular pressure by administering drugs which either reduce the production of aqueous humor within the eye or increase the fluid drainage, such as beta-blockers, α-agonists, cholinergic agents, carbonic anhydrase inhibitors, or prostaglandin analogs.

Several side effects are associated with the drugs conventionally used to treat glaucoma.

Topical beta-blockers show serious pulmonary side effects, depression, fatigue, confusion, impotence, hair loss, heart failure and bradycardia.

Topical α-agonists have a fairly high incidence of allergic or toxic reactions; topical cholinergic agents (miotics) can cause visual side effects.

The side effects associated with oral carbonic anhydrase inhibitors include fatigue, anorexia, depression, paresthesias and serum electrolyte abnormalities (The Merck Manual of Diagnosis and Therapy, Seventeenth Edition, M. H. Beers and R. Berkow Editors, Sec. 8, Ch. 100).

Finally, the topical prostaglandin analogs (bimatoprost, latanoprost, travoprost, tafluprost and unoprostone) used in the treatment of glaucoma can produce ocular side effects, such as increased pigmentation of the iris, ocular irritation, conjunctival hyperaemia, iritis, uveitis and macular oedema (Martindale, Thirty-third edition, p. 1445).

Diseases of the macula, such as age-related macular degeneration and diabetic macular edema, account for major causes of blindness. The drugs currently used for treating diseases of the macula are steroidal anti-inflammatory drugs such as triamcinolone acetonide or fluocinolone. However intravitreal triamcinolone injections are associated with many ocular complications including elevation of intraocular pressure.

Elevated intraocular pressure is a common post-surgical complications following ocular surgery such as pars plana vitrectomy, vitreoretinal surgery, retinal detachment surgery, panretinal photocoagulation.

It is known that in the eye nitric oxide (NO) has an important role in certain physiological processes, e.g. regulation of aqueous humor dynamics, vascular tone, retinal neurotransmission, retinal ganglion cell death by apoptosis, phototransduction and ocular immunological responses, on the other hand, the overproduction of NO is involved in several diseases of the eye.

U.S. Pat. No. 4,590,207 discloses ophthalmic solution containing isosorbide mononitrate as an active ingredient for treating and/or preventing intraocular hypertension and glaucoma.

US patent application 2002/0168424 discloses the use of a mixture of a nitric oxide (NO) donor such as nitrovasodilators like minoxidil, nitroglycerin, L-arginine, isosorbide dinitrate, or nitroprusside, and a cyclic guanosine 3',5'-monophosphate (cGMP) specific phosphodiesterase type 5 (PDE5) inhibitor such as sildenafil citrate for treating glaucoma or ocular hypertension. The disclosed combinations promote systemic vascular relaxation, enhanced blood flow to the optic nerve, dilation of the trabecular meshwork, the Schlemm's canal and uveoscleral outflow channel tissues, enhanced aqueous humor drainage and thus lowered intraocular pressure (IOP) in mammalian eye.

Organic nitrates have been used for over a century in the treatment of cardiac diseases however, it is known that the classical organic nitrates used in therapy, such as glycerol trinitrate, isosorbide dinitrate or isosorbide 5-mononitrate, undergo tolerance and lose their activity upon repeated administration. Nitrate tolerance develops despite an elevation in the drug plasma concentration reflecting a decrease in vascular sensitivity to previously therapeutic levels. This can be prevented or reduced by inclusion of a nitrate free period in the dosing schedule.

UK patent application no. GB 2 349 385 A discloses antioxidant nitrate or nitrite ester for use as vasodilator agents in the treatment of pathological conditions associated with endothelial dysfunction, in particular heart diseases.

The disclosed compounds contain a superoxide scavenger moiety and a nitrate or nitrite group and the two parts are stable linked in order to reduce the degradation of the molecules under physiological conditions. The stable link increases the activity of the anti-oxidant scavenger that can avert reactive oxygen species-mediated NO consumption of further production of deleterious species.

Therefore, the technical problem underlying the present invention is to provide effective therapeutic agents for the use in the treatment and/or prophylaxis of hypertensive glaucoma, normotensive glaucoma secondary glaucoma and ocular hypertension.

Surprisingly, it has now been found that the nitric oxide donors of the present invention lower intraocular pressure and develop significant inferior tolerance than that of nitric oxide donors described in the art.

It has also been surprisingly found that the nitric oxide donors of the present invention have additional beneficial anti-inflammatory and antioxidant properties that work synergistically with the delivery of nitric oxide to promote regulation of aqueous humor outflow through the trabecular meshwork, cells repairing and protection.

The present invention relates to compounds of formula (I) or stereoisomers thereof.

The present invention relates to compounds of formula (I)

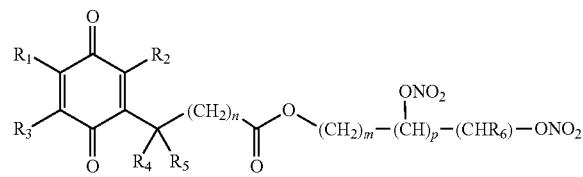

(I)

or stereoisomers thereof, wherein:
$R_1$ is selected from H, methyl, methoxy;
$R_2$ is H or methyl;
$R_3$ is selected from H, methyl, methoxy;
or $R_1$ and $R_3$ together form —CH=CH—CH=CH—;
$R_4$ and $R_5$ are methyl and n is 1, or
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 or 1;
$R_6$ is H or methyl.

Another embodiment of the invention provides a compound of formula (I) as above defined or stereoisomers thereof, wherein:
$R_1$ is selected from H, methyl, methoxy;
$R_2$ is methyl;
$R_3$ is selected from H, methyl, methoxy;
or $R_1$ and $R_3$ together form —CH=CH—CH=CH—;
$R_4$ and $R_5$ are methyl and n is 1,
m is an integer from 1 to 10, preferably m is an integer from 1 to 6, most preferably 4 or 6;
p is 0 or 1;
$R_6$ is H or methyl.

Another embodiment of the invention provides a compound of formula (I) as above defined or stereoisomers thereof, wherein:
$R_1$ is selected from H, methyl, methoxy;
$R_2$ is methyl;
$R_3$ is selected from H, methyl, methoxy;
or $R_1$ and $R_3$ together form —CH=CH—CH=CH—;
$R_4$ and $R_5$ are methyl and n is 1,
m is an integer from 1 to 10, preferably m is an integer from 1 to 6, most preferably 4 or 6;
p is 0 and $R_6$ is H.

Another embodiment of the invention provides a compound of formula (I) as above defined or stereoisomers thereof, wherein:
$R_1$ is selected from H, methyl, methoxy;
$R_2$ is methyl;
$R_3$ is selected from H, methyl, methoxy;
or $R_1$ and $R_3$ together form —CH=CH—CH=CH—;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 or 1;
$R_6$ is H or methyl.

Another embodiment of the invention provides a compound of formula (I) as above defined or stereoisomers thereof, wherein:
$R_1$ is selected from H, methyl, methoxy;
$R_2$ is methyl;
$R_3$ is selected from H, methyl, methoxy;
or $R_1$ and $R_3$ together form —CH=CH—CH=CH—;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 and $R_6$ is H.

Another embodiment of the invention provides a compound of formula (I) as above defined or stereoisomers thereof, wherein:
$R_1$ is selected from H, methyl, methoxy;
$R_2$ is methyl;
$R_3$ is selected from H, methyl, methoxy;
or $R_1$ and $R_3$ together form —CH=CH—CH=CH—;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 1 and $R_6$ is H or methyl, preferably $R_6$ is H.

Another embodiment of the invention provides a compound of formula (I) as above defined or stereoisomers thereof, wherein:
$R_1$, $R_2$ and $R_3$ are methyl;
$R_4$ and $R_5$ are methyl and n is 1;
m is an integer from 1 to 6, most preferably 4 or 6;
p is 0 or 1;
$R_6$ is H or methyl.

Another embodiment of the invention provides a compound of formula (I) as above defined or stereoisomers thereof, wherein:
$R_1$, $R_2$ and $R_3$ are methyl;
$R_4$ and $R_5$ are methyl and n is 1;
m is an integer from 1 to 6;
p is 0 and $R_6$ is H.

Another embodiment of the invention provides a compound of formula (I) as above defined or stereoisomers thereof, wherein:
$R_1$, $R_2$, $R_3$, are methyl;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 6, most preferably 4 or 6;
p is 0 or 1;
$R_6$ is H or methyl.

Another embodiment of the invention provides a compound of formula (I) or stereoisomers thereof, wherein:
$R_1$, $R_2$, $R_3$, are methyl;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 6, most preferably 4 or 6;
p is 0 and $R_6$ is H.

Another embodiment of the invention provides a compound of formula (I) as above defined or stereoisomers thereof, wherein:
$R_1$ is methoxy;
$R_2$ is methyl;
$R_3$ is methoxy;
$R_4$ and $R_5$ are methyl and n is 1;
m is an integer from 1 to 10, preferably m is an integer from 1 to 6, most preferably 4 or 6;
p is 0 or 1;
$R_6$ is H or methyl.

Another embodiment of the invention provides a compound of formula (I) as above defined
or stereoisomers thereof, wherein:
$R_1$ is methoxy;
$R_2$ is methyl;
$R_3$ is methoxy;
$R_4$ and $R_5$ are methyl and n is 1;
m is an integer from 1 to 10, preferably m is an integer from 1 to 6, most preferably 4 or 6;
p is 0 and $R_6$ is H.

Another embodiment of the invention provides a compound of formula (I) as above defined or stereoisomers thereof, wherein:
$R_1$ is methoxy;
$R_2$ is methyl;
$R_3$ is methoxy;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 or 1;
$R_6$ is H or methyl.

Another embodiment of the invention provides a compound of formula (I) as above defined or stereoisomers thereof, wherein:
$R_1$ is methoxy;
$R_2$ is methyl;
$R_3$ is methoxy;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 and $R_6$ is H.

Another embodiment of the invention provides a compound of formula (I) or stereoisomers thereof, wherein:
$R_2$ is methyl;
$R_1$ and $R_3$ together form —CH=CH—CH=CH—;
$R_4$ and $R_5$ are methyl and n is 1;
m is an integer from 1 to 10, preferably m is an integer from 1 to 6, most preferably 4 or 6;
p is 0 or 1;
$R_6$ is H or methyl.

Another embodiment of the invention provides a compound of formula (I) as above defined or stereoisomers thereof, wherein:
$R_2$ is methyl;
$R_1$ and $R_3$ together form —CH=CH—CH=CH—;
$R_4$ and $R_5$ are methyl and n is 1;
m is an integer from 1 to 10, preferably m is an integer from 1 to 6, most preferably 4 or 6;
p is 0 and $R_6$ is H.

Another embodiment of the invention provides a compound of formula (I) as above defined or stereoisomers thereof, wherein:
$R_2$ is methyl;
$R_1$ and $R_3$ together form —CH=CH—CH=CH—;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 or 1;
$R_6$ is H or methyl.

Another embodiment of the invention provides a compound of formula (I) as above defined or stereoisomers thereof, wherein:
$R_2$ is methyl;
$R_1$ and $R_3$ together form —CH=CH—CH=CH—;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 and $R_6$ is H.

Another embodiment of the invention provides a compound of formula (I) as above defined
or stereoisomers thereof, wherein:
$R_1$ is methyl;
$R_2$ is methyl;
$R_3$ is methoxy;
$R_4$ and $R_5$ are methyl and n is 1;
m is an integer from 1 to 10, preferably m is an integer from 1 to, most preferably 4 or 6;
p is 0 or 1;
$R_6$ is H or methyl.

Another embodiment of the invention provides a compound of formula (I) as above defined or stereoisomers thereof, wherein:
$R_1$ is methyl;
$R_2$ is methyl;
$R_3$ is methoxy;
$R_4$ and $R_5$ are methyl and n is 1;
m is an integer from 1 to 10, preferably m is an integer from 1 to 6, most preferably 4 or 6;
p is 0 and $R_6$ is H.

Another embodiment of the invention provides a compound of formula (I) as above defined or stereoisomers thereof, wherein:
$R_1$ is methyl;
$R_2$ is methyl;
$R_3$ is methoxy;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 or 1;
$R_6$ is H or methyl.

Another embodiment of the invention provides a compound of formula (I) as above defined or stereoisomers thereof, wherein:

$R_1$ is methyl;
$R_2$ is methyl;
$R_3$ is methoxy;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 and $R_6$ is H.

Another embodiment of the invention provides a compound of formula (I) as above defined or stereoisomers thereof, wherein:
$R_1$ is methoxy;
$R_2$ is methyl;
$R_3$ is methyl;
$R_4$ and $R_5$ are methyl and n is 1;
m is an integer from 1 to 10, preferably m is an integer from 1 to 6, most preferably 4 or 6;
p is 0 or 1;
$R_6$ is H or methyl.

Another embodiment of the invention provides a compound of formula (I) as above defined or stereoisomers thereof, wherein:
$R_1$ is methoxy;
$R_2$ is methyl;
$R_3$ is methyl;
$R_4$ and $R_5$ are methyl and n is 1;
m is an integer from 1 to 10, preferably m is an integer from 1 to 6, most preferably 4 or 6;
p is 0 and $R_6$ is H.

Another embodiment of the invention provides a compound of formula (I) as above defined or stereoisomers thereof, wherein:
$R_1$ is methoxy;
$R_2$ is methyl;
$R_3$ is methyl;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 or 1;
$R_6$ is H or methyl.

Another embodiment of the invention provides a compound of formula (I) as above defined or stereoisomers thereof, wherein:
$R_1$ is methoxy;
$R_2$ is methyl;
$R_3$ is methyl;
$R_4$ is H, $R_5$ is selected from phenyl, para-fluorophenyl, para-methoxyphenyl, para-isopropylphenyl, para-trifluoromethylphenyl and para-methylphenyl and n is 2;
m is an integer from 1 to 10, preferably m is an integer from 1 to 6, most preferably 4 or 6;
p is 0 and $R_6$ is H.

Another embodiment of the invention provides a compound of formula (I) selected from the group:

(7)
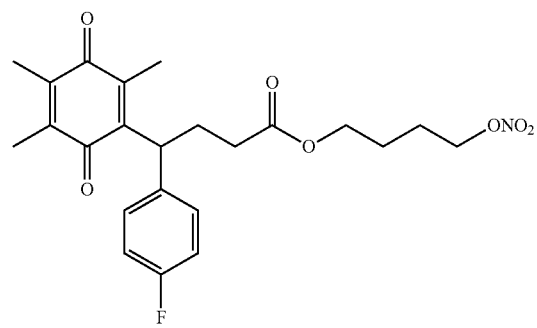

(8)
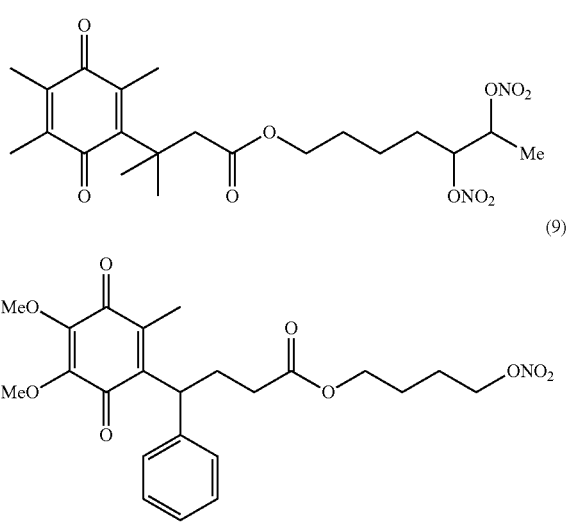

(9)
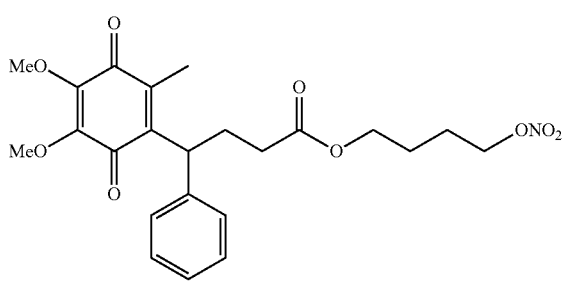

(10)
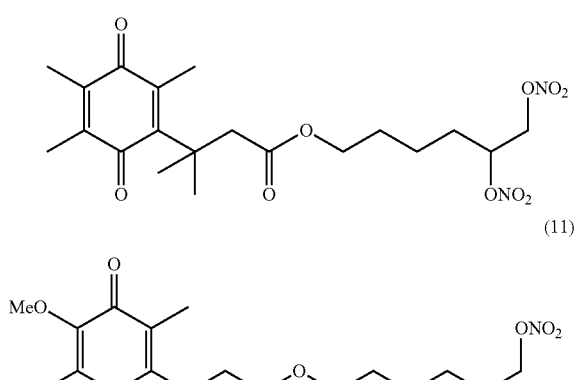

(11)
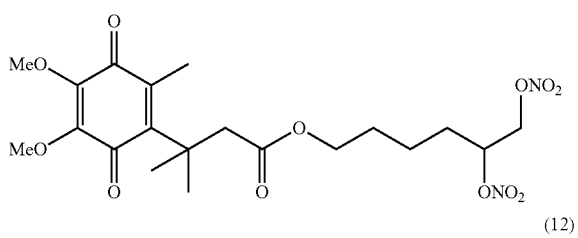

(12)
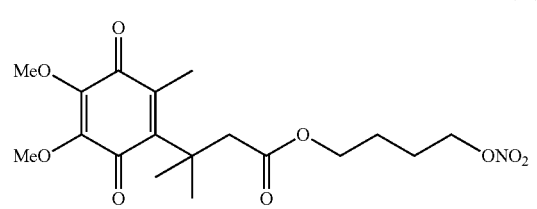

(13)
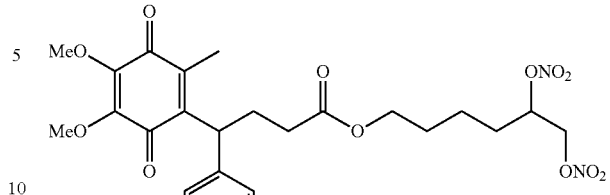

(14)
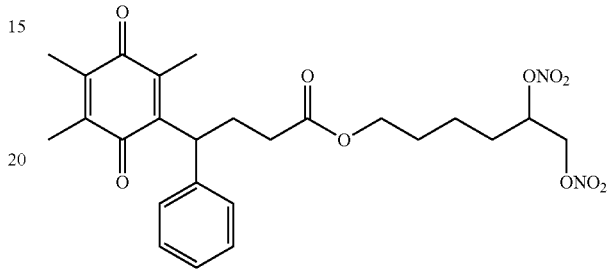

(15)
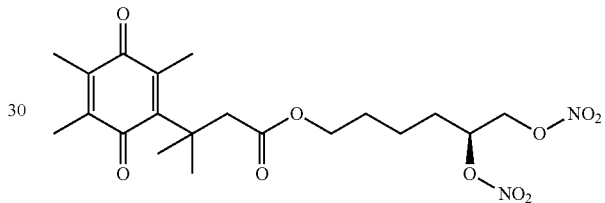

(16)
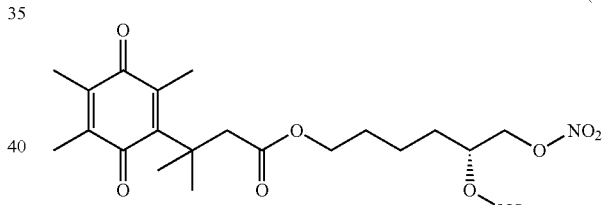

(17)
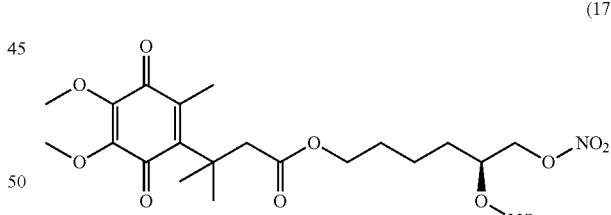

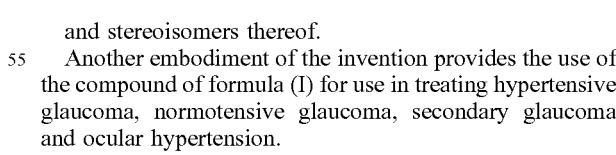

and stereoisomers thereof.

Another embodiment of the invention provides the use of the compound of formula (I) for use in treating hypertensive glaucoma, normotensive glaucoma, secondary glaucoma and ocular hypertension.

The tests performed demonstrated that compounds of formula (I) show an antioxidant activity comparable with that of well known antioxidant compounds like ferulic and caffeic acid or edaravone.

Moreover the compounds of the present invention significantly attenuated the saline-induced IOP rise in an in vivo model of transient ocular hypertension in rabbit.

Consequently, the compounds of the invention may be used as drug for the prevention and/or treatment of ocular pathologies where not only a deficit of NO but also oxidative stress play an important role in their pathogenesis.

Another embodiment of the present invention relates to compounds of formula (I) for the treatment and/or prophylaxis of hypertensive glaucoma, normotensive glaucoma secondary glaucoma and ocular hypertension.

Another embodiment of the present invention to compounds of formula (I) for the treatment of high intraocular pressure resulting from orbital edema, post-surgical complications, intraocular inflammation, pupillary block or idiopathic causes.

Furthermore the present invention relates to compounds of formula (I) for the use in the treatment and/or prophylaxis of age related macular degeneration, diabetic retinopathy, retinal vein occlusion, macular degeneration, inflammatory retinal disease, uveitis.

The present inventions also relates to compositions comprising a nitric oxide donor of formula (I) in combination with one or more further active ingredients selected from the group consisting of alpha adrenergic agonist, beta blocker, carbonic anhydrase inhibitor, prostaglandin analogs, non-steroidal anti-inflammatory drugs, steroidal anti-inflammatory drugs.

Examples of suitable alpha adrenergic agonists are brimonidine, apraclonidine, clonidine.

Examples of suitable beta blockers are timolol, carteolol, betaxolol, levobunolol.

Examples of suitable carbonic anhydrase inhibitors are dorzolamide, acetazolamide, brinzolamide, dorzolamide, dichlorphenamide, methazolamide.

Examples of suitable prostaglandin analogs are bimatoprost, latanoprost, travoprost, unoprostone and tafluprost.

Examples of non-steroidal anti-inflammatory drugs are bromfenac, flurbiprofen, naproxen, ketoprofen.

Examples of steroidal anti-inflammatory drugs are dexamethsone, fluocinolone acetonide, triamcinolone acetonide, budesonide, prednisolone.

Another embodiment of the present invention is a composition above reported for use in the treatment and/or prophylaxis of hypertensive glaucoma, normotensive glaucoma, secondary glaucoma and ocular hypertension.

Another embodiment of the present invention is a composition above reported for use in the treatment and/or prophylaxis of secondary glaucomas, age related macular degeneration, diabetic retinopathy, macular degeneration, inflammatory retinal disease, uveitis.

Another embodiment of the present invention is a composition above reported for use in the treatment of high intraocular pressure resulting from orbital edema, post-surgical complications, intraocular inflammation, pupillary block, or idiopathic causes.

Another embodiment of the present invention provides pharmaceutical formulation for topical, periocular or intraocular administration comprising at least a nitric oxide donor of formula (I) and at least an ophthalmically acceptable component and/or ophthalmic ally acceptable vehicle.

Another embodiment of the present invention provides pharmaceutical formulation for topical, periocular or intraocular administration comprising at least a nitric oxide donor of formula (I) one or more further active ingredients selected from the group consisting of alpha adrenergic agonist, beta blocker, carbonic anhydrase inhibitor, prostaglandin analogs, non-steroidal anti-inflammatory drugs, steroidal anti-inflammatory drugs and at least an ophthalmically acceptable component and/or ophthalmically acceptable vehicle.

The preferred route of administration of the compounds and compositions of the present invention is topical or intravitreal. The compounds and compositions of the present invention can be administered as solutions, suspensions, or emulsions (dispersions) for topical use.

The compounds for use in the current invention can also be administered via periocular administration, and may be formulated in solutions or suspensions for periocular administration. Formulations useful for periocular administration will generally be periocular injection formulations or surgical irrigating solutions. Periocular administration refers to administration to tissues near the eye, such as administration to the tissues or spaces surrounding the eyeball and within the orbit. Periocular administration can take place by injection, deposit, or any other mode of placement.

The compounds and the compositions of the present invention compositions may be formulated in solutions or suspensions for intraocular administration. Compositions useful for intraocular administration will generally be intraocular injection compositions or surgical irrigating solutions.

An "ophthalmically acceptable" component refers to a component which will not cause any significant ocular damage or ocular discomfort at the intended concentration and over the time of intended use. Solubilizers and stabilizers should be non-reactive. An "ophthalmically acceptable vehicle" refers to any substance or combination of substances which are non-reactive with the compounds and suitable for administration to a patient.

The nitric oxide donors of the present invention will generally be contained in the topical, periocular, or intraocular formulations contemplated herein in an amount of from about 0.001 to about 10.0% weight/volume. Preferred concentrations will range from about 0.1 to about 5.0% w/v.

General Synthesis

The compounds of formula (I) wherein $R_1$, $R_2$, $R_3$, $R_6$, m and p are as above defined, $R_4$ and $R_5$ are methyl n is 1 can be prepared:

by reacting compounds (Va) with compounds of formula (VI) wherein $R_6$, m and p are as above defined, in presence of coupling reagents such as DCC, EDC, HBTU, HATU, and of catalytic amount of DMAP or $Sc(OTf)_3$ in an aprotic/non polar solvent such as THF, DMF or $CH_2Cl_2$ or at temperature ranging from $-80°$ C. to $60°$ C. as depicted in Scheme 1; or by reacting compounds of formula (Vb), wherein Xa is an activating group selected from $N_3$, F, Cl, Br, or a group depicted in Formulas ((Xaa) or (Xbb),

(Xaa)

(Xbb)

preferably Cl or (Xaa), with compounds (VI) in presence of a base such as DMAP, pyridine or triethylamine or $K_2CO_3$, $Cs_2CO_3$ in an aprotic/non polar solvent such as THF, DMF or $CH_2Cl_2$ or at temperature ranging from −80° C. to 60° C. as depicted in Scheme 1:

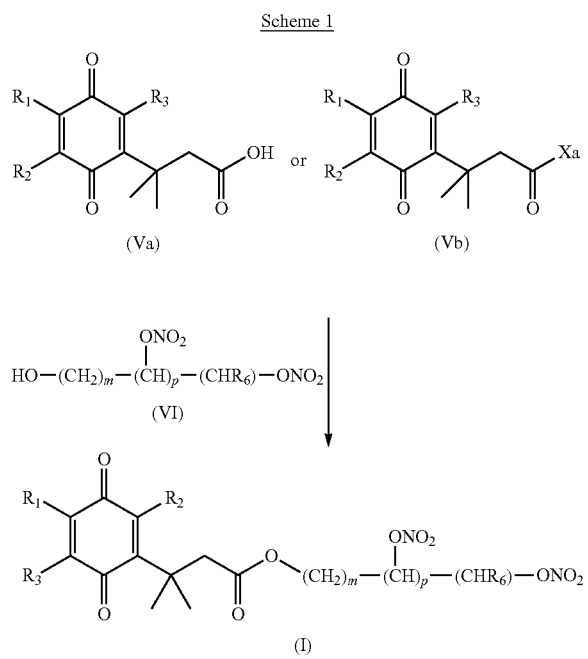

Compounds of formula (Vb) can be prepared by known method from the corresponding compounds of formula (Va). Compounds of formula (Va) can be generally prepared as depicted in Scheme 2 following the method described by Carpino et al., J. Org. Chem., 1989, 54, 3303-3310.

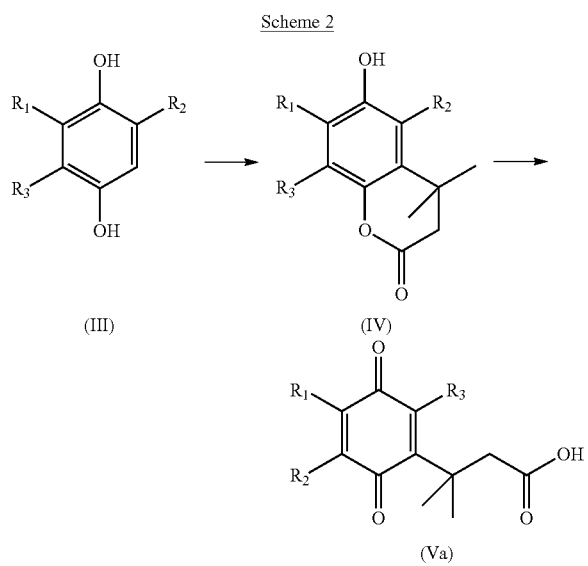

Hydroquinones of general formula (III) are reacted with methanesulfonic acid and methyl 3-methylbut-2-enoate to obtain the lactones (IV) as described in literature by Carpino et al., J. Org. Chem., 1989, 54, 3303-3310.

Compounds of formula (Va) are prepared by reacting compounds (IV) with an oxidant such as freshly crystallized NBS or PDC according to conditions described by Borchardt et al., J. Am. Chem. Soc., 1972, 94, 9175 and Carpino et al., J. Org. Chem., 1989, 54, 3303-3310.

Compounds of formula (III) are commercially available or can be prepared by reduction of the corresponding quinones of formula (II), using reducing reagents such as, for example $NaBH_4$ in methanol (Scheme 3).

Quinones of formula (II) are commercially available or can be prepared by methods described in the literature.

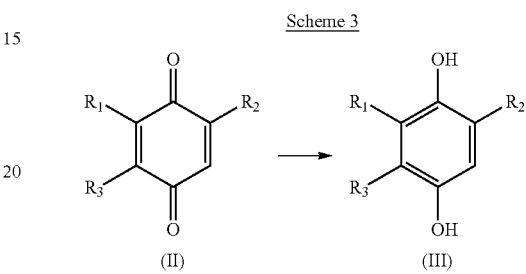

Compounds of formula (VI) wherein m, p and $R_6$ are as above defined, are known in the literature or can be synthesized starting from the corresponding alcohols of formula (VIIa)

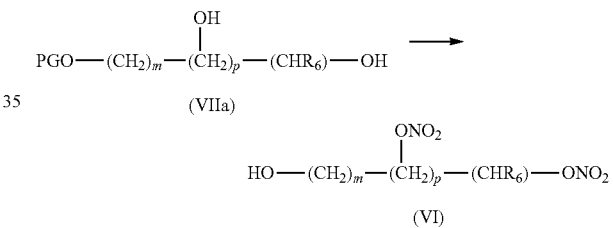

wherein PG is a suitable hydroxyl protective group, preferably an ester such as a benzoic ester, and m, p and $R_6$ are as above defined by reaction with nitric acid and acetic anhydride in a temperature range from −50° C. to 20° C., or by reacting with triflic anhydride/tetraalkylammonium nitrate salt in an aprotic polar/non polar solvent such as DMF, THF or CH2Cl2 at temperature ranging from −80° C. to 65° C. in the presence of a base as pyridine, lutidine, 2,6-di-tert-butyl-4-methylpyridine followed by the removal of the protective group by known methods (see for example: T. W. Greene, P. G. M. Wuts "Protective groups in organic Synthesis", 4th edition, J. Wiley & Sons, New York, 2006).

Alternatively, the hydroxyl group of (VIIa) are first converted to the corresponding mesyl or tosyl or triflate group and then nitrated using known methods, as for example tetraalkylammonium nitrate and sodium nitrate followed by the removal of the protecting group by methods well known in the art.

Alternatively compounds of formula (VI) wherein m and $R_6$ are as above defined, p is 0 can be synthesized by reacting the corresponding halogen derivative (VIIb) wherein Q is H or PG wherein PG is as previously defined and X is an halogen atom as Cl, Br, I with a nitrating agent, for example, $AgNO_3$ in acetonitrile as known in the literature, followed by the removal of the Q protecting group, when present, by methods well known in the art.

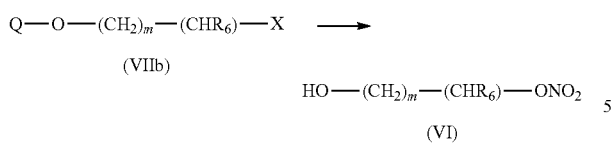

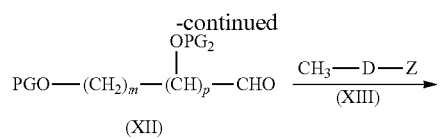

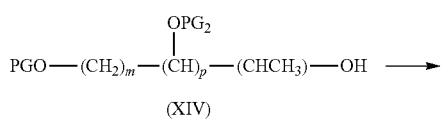

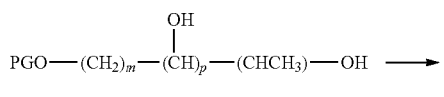

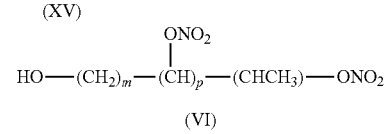

Compound of formula (VIIa) wherein m is as previously defined, p is 1 and $R_6$ is H or $CH_3$ can be synthesized by reacting the corresponding alkenyl-alcohol of formula (VIIIb) with a dihydroxylating reagent such as ADmixα or ADmixβ or $KMnO_4$, $OsO_4$ in a 1/1 mixture of protic/aprotic solvents like tBuOH, $H_2O$, optionally in the presence of an activator like methanesulfonamide at temperature ranging from −20 to 30° C., optionally followed by a chiral separation of the diols (VIIa)

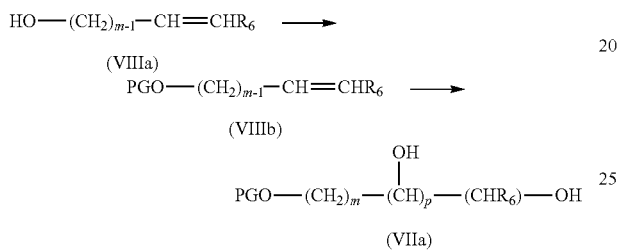

Compounds of formula (VIIIb) are prepared from compounds (VIIIa) by protecting the free hydroxyl group with a suitable PG group already defined with known methods (see for example: T. W. Greene, P. G. M. Wuts "Protective groups in organic Synthesis", 4th edition, J. Wiley & Sons, New York, 2006).

Compounds (VIIa) are commercially available or can be prepared from known compounds using known methods.

Alternatively compounds (VI) wherein m is as above defined, p is 1 and $R_6$ is H can be prepared by reacting compounds (VIIIb) with $I_2$ and $AgNO_3$ in acetonitrile as described in the literature (see Cena, C. et al in *Bioorganic & Medicinal Chemistry* 2008, 16, 5199-5206.

Alternatively compounds (VI) wherein m is as above defined, p is 1 and $R_6$ is $CH_3$ can be obtained from compounds (VIIa) as depicted in Scheme 4, according the following steps:

Scheme 4

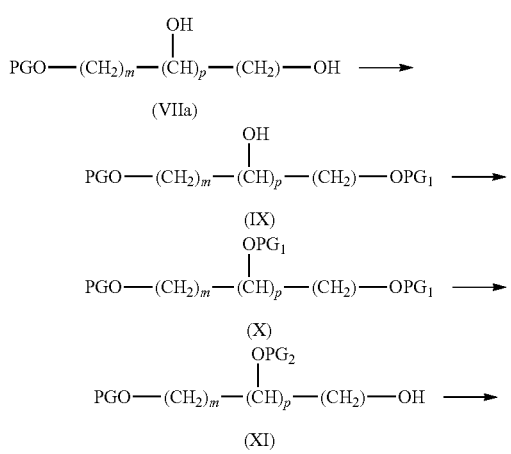

1) protecting the primary hydroxyl group of compounds (VIIa)

2) protecting the secondary hydroxyl group to obtain compounds of formula (X) wherein $PG_1$ is the trityl group and $PG_2$ is TBDPS, TBDMS or TIPS.

3) removing the protecting group $PG_1$ and oxidizing compound (XI) to aldehyde with known methods to obtain compounds (XII)

4) reacting compound (XII) with compound (XIII)

$$CH_3\text{-}D\text{-}Z_2 \quad (XIII)$$

wherein D is Zn, Mg, or Cu, preferably Zn; Z is R or a halogen, preferably Cl, in the presence of a chiral amino alcohol catalyst such as (1S,2R)-(−)-(dibutylamino)-1-phenyl-1-propanol or (1R,2S)-(+)-(dibutylamino)-1-phenyl-1-propanol or an achiral catalyst in an aprotic/non polar solvent such as toluene, THF or $Et_2O$ at temperature ranging from −80° C. to 65° C.

5) removing the protecting group $PG_2$ by methods well known in the art to obtain compound (VI).

Compounds of formula (I) wherein $R_4$ is H and $R_5$ is selected from phenyl, para-fluorophenyl, para-methoxyphenyl, para-isopropylphenyl, para-trifluoromethylphenyl and para-methylphenyl, n is 2 and $R_1$, $R_2$, $R_3$, $R_6$ m and p are as above defined, can be prepared:

by reacting compounds of formula (XVIIIa) wherein $R_1$, $R_2$, $R_3$ are as above defined, $R_8$ is H, F, $CH_3O$—, $(CH_3)_2CH$—, $CF_3$— or $CH_3$—, with compounds of formula (VI) as above defined, in presence of a coupling reagent such as DCC, EDC, HBTU, HATU, and of catalytic amount of $Sc(OTf)_3$ or DMAP, as depicted in scheme 5;

by reacting compounds of formula (XVIIIb) wherein $R_1$, $R_2$, $R_3$, $R_8$ and Xa are as above defined, with compounds of formula (VI) in presence of a base such as DMAP pyridine or triethylamine or $K_2CO_3$, $Cs_2CO_3$ in an aprotic/non polar solvent such as THF, DMF or $CH_2Cl_2$ or at temperature ranging from −80° C. to 60° C. as depicted in Scheme 5:

Scheme 5

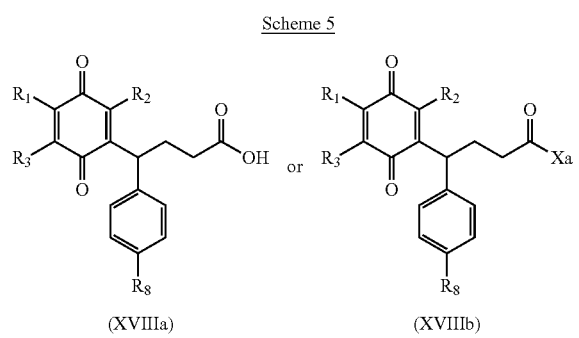

(XVIIIa)    (XVIIIb)

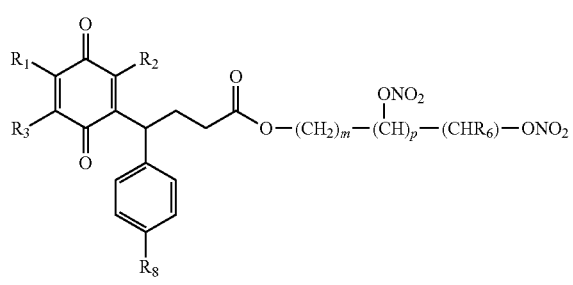

(I)

Compounds of formula (XVIIIb) can be obtained using known methods starting from the corresponding compounds of formula (XVIIIa).

Compound of formula (XVIIIa) can be prepared by oxidation of carboxylic acids of formula (XVII) wherein $R_1$, $R_2$, $R_3$ and $R_8$ are as above described according to the procedure disclosed by Jurd and Wong, Aust. J. Chem. 1980, 33, 137, as depicted in Scheme 6.

Carboxylic acids of formula (XVII) can be prepared by acid-catalyzed coupling reaction between hydroquinone (III) and the commercially available γ-lactone (XVI)

Scheme 6

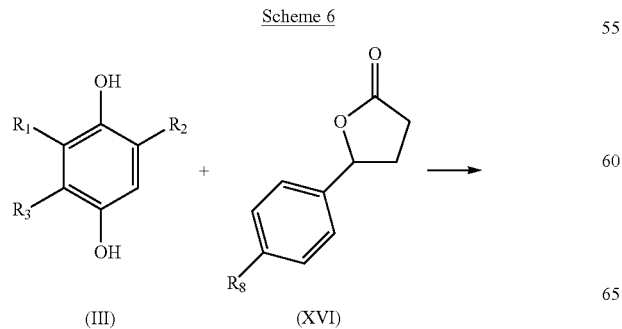

(III)    (XVI)

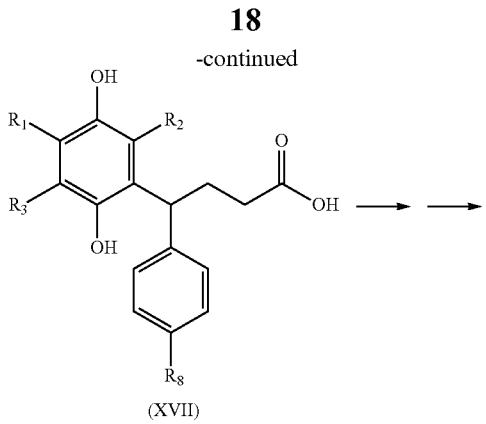

(XVII)

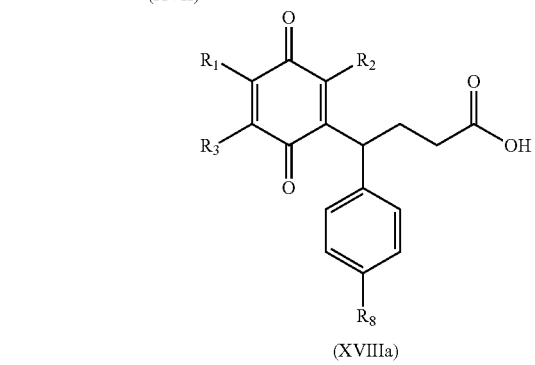

(XVIIIa)

Example 1

Synthesis of 4-(nitrooxy)butyl 3-methyl-3-(2,4,5-trimethyl-3,6-dioxocyclohexa-1,4-dienyl)butanoate (Compound 1)

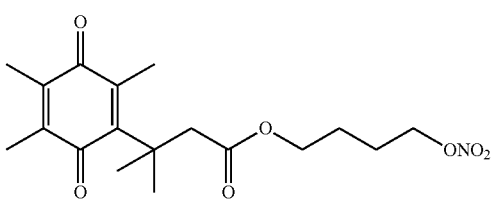

Step 1: Synthesis of 6-hydroxy-4,4,5,7,8-pentamethylchroman-2-one

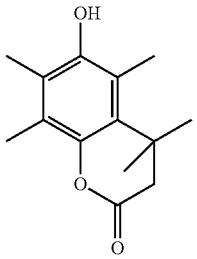

A synthetic procedure similar to the one described by Carpino et al., J. Org. Chem., 1989, 54, 3303-3310 was used. Methanesulfonic acid (20 mL) was heated at 70° C. In parallel, 2,3,5-trimethylbenzene-1,4-diol (2.0 g, 13.14 mmol) and methyl 3-methylbut-2-enoate (1.94 mL, 13.14 mmol, 1 eq) were added quickly and the reaction was heated for 2 h at this temperature. The reaction was then poured in water and, after cooling, was extracted with EtOAc (3×100 mL). The combined organic layers were washed successively with water, saturated NaHCO$_3$, water and brine, dried (Na$_2$SO$_4$), filtered and evaporated. The residue was crystallized from 30% CHCl$_3$ in n-Hexane to give the title compound as a pale grey solid (1.86 g, Yield: 60%). Melting point: 185° C.

$^1$H NMR (300 MHz, CDCl$_3$) δ 4.63 (s, 1H), 2.54 (s, 2H), 2.36 (s, 3H), 2.22 (s, 3H), 2.18 (s, 3H), 1.45 (s, 6H).

Step 2: Synthesis of 3-methyl-3-(2,4,5-trimethyl-3,6-dioxocyclohexa-1,4-dien-1-yl)butanoic acid (Intermediate 2)

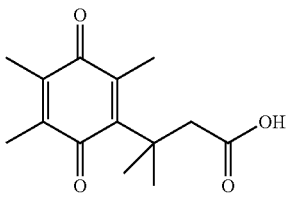 [SMILES: CC1=C(C)C(=O)C(C(C)(C)CC(=O)O)=C(C)C1=O]

The reaction was performed according to conditions described by Borchardt et al., J. Am. Chem. Soc., 1972, 94, 9175.

A stirred solution of 6-hydroxy-4,4,5,7,8-pentamethylchroman-2-one (2.0 g, 0.853 mmol) in 10% aqueous acetonitrile (100 mL) was added with a solution of freshly recrystallised NBS (1.6 g, 0.853 mmol, 1 eq) in acetonitrile (20 mL). The reaction was stirred for 1 h and then diluted with water (100 mL) and extracted with Et$_2$O (3×100 mL). The combined organic layers were washed with water and brine, dried (Na$_2$SO$_4$), filtered and evaporated. The residue was crystallized from Et$_2$O/n-Hexane to give the title compound as a yellow solid (1.64 g, Yield: 77%).

$^1$H NMR (300 MHz, CDCl$_3$) δ 11.08-8.78 (m, 1H), 3.02 (s, 2H), 2.14 (s, 3H), 1.95 (s, 3H), 1.93 (s, 3H), 1.44 (s, 6H).

Step 3: Synthesis of 4-hydroxybutyl 4-nitrobenzoate

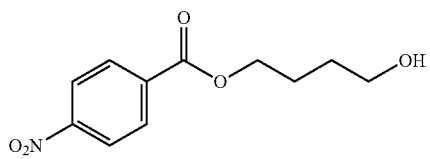 [SMILES: O=C(OCCCCO)c1ccc([N+](=O)[O-])cc1]

A stirred solution of 1,4-butandiol (3.0 g, 33.29 mmol, 1.1 eq) and 4-nitrobenzoyl chloride (5.56 g, 29.96 mmol) in EtOAc (100 mL) cooled to 0° C. was added dropwise with triethylamine (4.6 mL, 33.3 mmol, 1.1 eq) and the reaction was stirred vigorously for 6 h. The reaction was diluted with water and the organic layer separated, washed with HCl 0.1 M, water and brine. The organic phase was dried (Na$_2$SO$_4$), filtered and evaporated. The residue was triturated in cold Et$_2$O and the solid filtered off. The filtrate was evaporated to give the title compound as a viscous oil which solidified upon standing (2.86 g, Yield: 40%).

$^1$H NMR (300 MHz, CDCl$_3$) δ 8.30 (d, J=8.8, 2H), 8.22 (d, J=8.8, 2H), 4.44 (t, J=6.5, 2H), 3.76 (t, J=6.3, 2H), 1.93 (dt, J=14.4, 6.7, 2H), 1.75 (dt, J=13.2, 6.4, 2H).

Step 4: Synthesis of 4-(nitrooxy)butyl 4-nitrobenzoate

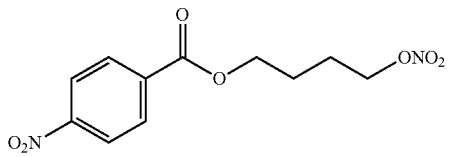

Concentrated nitric acid (1.9 mL, 45.15 mmol, 3 eq) was added dropwise to acetic anhydride (20 mL) cooled to 0° C. Then solid 4-hydroxybutyl 4-nitrobenzoate was added and the reaction was stirred at this temperature for 30 min then poured on ice. After melting, the organic oil was separated from the aqueous liquid and diluted with EtOAc. The organic layer was washed with NaHCO3 (2×30 mL), water and brine, dried (Na2SO4), filtered and evaporated. The residue was purified by flash chromatography (Biotage System, SNAP Cartridge silica 100 g, eluent: n-hexane/ethyl acetate 85/15 to n-hexane/ethyl acetate 75/25 during 8 CV) affording the title compound as a yellow oil (3.73 g, Yield: 87%).

$^1$H NMR (300 MHz, CDCl$_3$) δ 8.34-8.29 (m, 2H), 8.24-8.19 (m, 2H), 4.56 (t, J=5.9, 2H), 4.44 (t, J=6.0, 2H), 1.99-1.90 (m, 4H).

Step 5: Synthesis of 4-hydroxybutyl nitrate

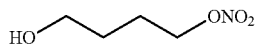

A stirred solution of 4-(nitrooxy)butyl 4-nitrobenzoate (2.13 g, 7.49 mmol) in a 3/1 THF/EtOH mixture (40 mL) cooled to 0° C. was added with NaOH 1M (7.5 mL, 1 eq). The reaction was stirred at this temperature for 3 h then diluted with EtOAc and water. The organic layer was separated, washed with water and brine, dried (Na$_2$SO$_4$), filtered and evaporated. The residue was purified flash chromatography (Biotage System, SNAP Cartridge silica 100 g, eluent: n-hexane/ethyl acetate 85/15 to n-hexane/ethyl acetate 75/25 during 8 CV) affording the title compound as a colourless oil (0.48 g, Yield: 49%).

$^1$H NMR (300 MHz, CDCl$_3$) δ 4.52 (t, J=6.5, 2H), 3.72 (t, J=6.2, 2H), 1.87 (dt, J=14.2, 6.5, 2H), 1.75-1.63 (m, 1H).

Step 6: Synthesis of 4-(nitrooxy)butyl 3-methyl-3-(2,4,5-trimethyl-3,6-dioxocyclohexa-1,4-dienyl)butanoate (Compound 1)

A stirred solution of 4-hydroxybutyl nitrate (prepared in Step 5) (2.0 g, 14.8 mmol) and 3-methyl-3-(2,4,5-trimethyl-3,6-dioxocyclohexa-1,4-dien-1-yl)butanoic acid (prepared in Step 2) (3.70 g, 14.8 mmol) in dry CH$_2$Cl$_2$ cooled to 0° C. was added with EDC (3.12 g, 16.28 mmol, 1.1 eq) and a catalytic amount of DMAP (0.05 g). The reaction was stirred for 5 h at this temperature and then washed with water, HCl 1M, water and brine, dried (Na$_2$SO$_4$), filtered and evaporated. The residue was purified by flash chromatography (Biotage System, 2 SNAP Cartridge silica 340 g, eluent: n-hexane/ethyl acetate 85/15 to n-hexane/ethyl acetate 70/30 during 8 CV) affording the title compound as a yellow oil (5.02 g, Yield: 92%).

$^1$H NMR (300 MHz, CDCl$_3$) δ 4.45 (t, J=6.2, 2H), 4.01 (t, J=6.1, 2H), 2.98 (s, 2H), 2.14 (s, 3H), 1.94 (s, 6H), 1.82-1.62 (m, 4H), 1.42 (s, 6H).

Example 2

Synthesis of 6-(nitrooxy)hexyl 3-methyl-3-(2,4,5-trimethyl-3,6-dioxocyclohexa-1,4-dienyl)butanoate (Compound 2)

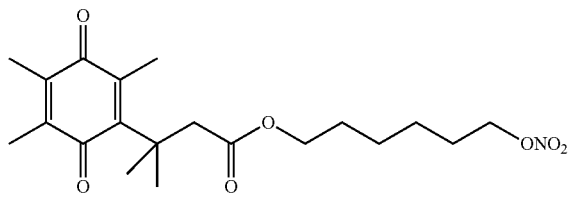

Step 1: Synthesis of 6-Nitrooxy-hexan-1-ol

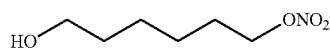

A solution of 6-bromohexan-1-ol (2.2 mL, 16.6 mmol) in CH$_3$CN (100 mL) was added with silver nitrate (5.95 g, 35 mmol, 2 eq). The reaction was stirred at room temperature for 3 days. The reaction was quenched by addition of a solution of brine. After 15 min of stirring, the solution was filtered, extracted with ethyl acetate, washed with H$_2$O, brine, dried over sodium sulfate, filtered and evaporated. The residue was purified by column chromatography (Biotage System, SNAP Cartridge silica 100 g, eluent: n-hexane/ethyl acetate 80/20 to n-hexane/ethyl acetate 50/50 during 12 CV) to give the desired product as a colorless oil (2.34 g, Yield: 86%).

$^1$H NMR (300 MHz, CDCl$_3$) 4.47 (t, J=6.6 Hz, 2H), 3.68 (t, J=6.1 Hz, 2H), 1.77 (m, 2H), 1.62 (m, 2H), 1.48 (m, 4H), 1.27 (s, 1H).

Step 2: Synthesis of 6-(nitrooxy)hexyl 3-methyl-3-(2,4,5-trimethyl-3,6-dioxocyclohexa-1,4-dienyl)butanoate A stirred solution of 6-hydroxyhexyl nitrate (164 mg, 1.0 mmol) and 3-methyl-3-(2,4,5-trimethyl-3,6-dioxocyclohexa-1,4-dien-1-yl)butanoic acid (prepared in Example 1, Step 2) (250 mg, 1.0 mmol) in dry CH2Cl2 cooled to 0° C. was added with EDC (202 mg, 1.1 mmol, 1.1 eq) and a catalytic amount of DMAP (0.02 g). The reaction was stirred for 16 h from 0° C. to rt. The reaction was washed with water, HCl 1M, water and brine, dried (Na$_2$SO$_4$), filtered and evaporated. The residue was purified by flash chromatography (Biotage System, SNAP Cartridge silica 100 g, eluent: n-hexane/ethyl acetate 85/15 to n-hexane/ethyl acetate 70/30 during 8 CV) affording the title compound as a yellow oil (286 mg, Yield: 72%).

$^1$H NMR (300 MHz, CDCl$_3$) δ 4.44 (t, J=6.6, 2H), 3.97 (t, J=6.6, 2H), 2.97 (s, 2H), 2.12 (s, 3H), 1.94 (d, J=10.4, 6H), 1.77-1.65 (m, 2H), 1.63-1.50 (m, 2H), 1.47-1.41 (m, 6H), 1.41-1.30 (m, 4H).

Example 3

Synthesis of 6-(nitrooxy)hexyl 4-phenyl-4-(2,4,5-trimethyl-3,6-dioxocyclohexa-1,4-dienyl)butanoate (Compound 3)

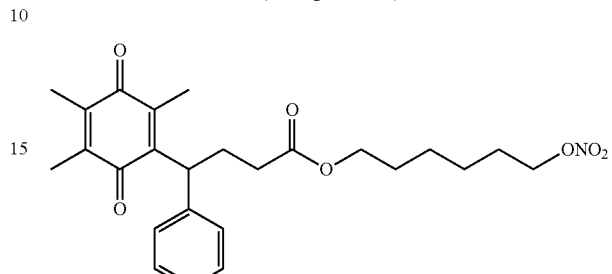

Step 1: Synthesis of 4-(2,5-dihydroxy-3,4,6-trimethylphenyl)-4-phenylbutanoic acid

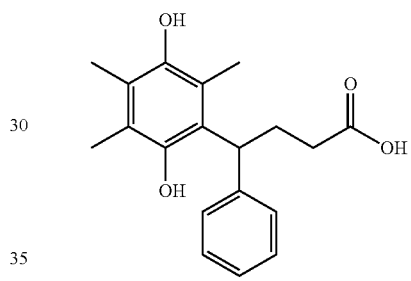

The reaction was performed according to conditions described by Mitsuru et al., J. Med. Chem. Soc., 1989, 32, 2214-2221.

Boron trifluoride etherate (0.25 ml; 1.99 mmol) was added dropwise to a mixture of trimethylhydroquinone (1.0 g; 6.57 mmol) and γ-phenyl-γ-butyrolactone (1.1 g; 6.57 mmol) in toluene (70 ml) at 60° C. during 10 minutes. The mixture was stirred for further 2 hours and then the solvent was evaporated under reduced pressure. The residue was purified by flash chromatography (Biotage system, SNAP Cartridge silica 100 g, EtOAc in n-hexane from 9% to 60% in 10 CV) affording the title compound (0.74 g; Yield: 36%) as an orange solid.

$^1$H NMR (300 MHz, CDCl$_3$) δ 7.39-7.07 (m, 5H), 4.72-4.25 (m, 3H), 2.74-2.25 (m, 4H), 2.25 (s, 3H), 2.08 (s, 3H), 1.98 (m, 2H).

Step 2: Synthesis of 4-phenyl-4-(2,4,5-trimethyl-3,6-dioxocyclohexa-1,4-dien-1-yl)butanoic acid

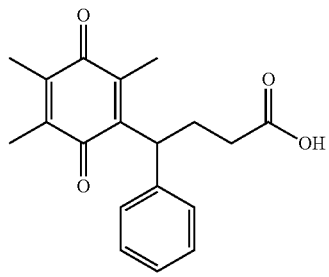 [SMILES: CC1=C(C)C(=O)C(C(CCC(=O)O)c2ccccc2)=C(C)C1=O]

To a solution of 4-(2,5-dihydroxy-3,4,6-trimethylphenyl)-4-phenylbutanoic acid (0.74 g; 2.33 mmol) in CH$_3$CN:H$_2$O 1:1 (50 ml), Ammonium cerium nitrate (3.3 g; 5.87 mmol) was added. The mixture was stirred 3 hours at room temperature then was poured into H$_2$O (30 ml). Et$_2$O (20 ml) was added, the two phases were separated and the organic layer was extracted with Et$_2$O (2×20 ml). The combined organic layers were washed with brine, dried on Na$_2$SO$_4$ and concentrated affording 560 mg of the title compound without any further purification.

$^1$H NMR (300 MHz, CDCl$_3$) δ 7.40-7.06 (m, 5H), 4.35 (t, J=7.6, 1H), 2.77-2.25 (m, 4H), 2.15-2.03 (m, 3H), 1.97 (m, 6H).

Step 3: Synthesis of 6-(nitrooxy)hexyl 4-phenyl-4-(2,4,5-trimethyl-3,6-dioxocyclohexa-1,4-dienyl)butanoate (compound (3))

To a solution of 4-phenyl-4-(2,4,5-trimethyl-3,6-dioxocyclohexa-1,4-dien-1-yl)butanoic acid (0.29 g; 0.92 mmol) and 6-Nitrooxy-hexan-1-ol (synthesised in Example 2, step 1) (0.17 mg; 0.92 mmol) in CH$_2$Cl$_2$ (5 ml), 1-Ethyl-3-(3-dimethylaminopropyl) carbodiimide (EDC) (0.29 g; 1.38 mmol) and DMAP cat. were added. The solution was stirred 30 minutes at 0° C. and 4 hours at room temperature then washed with a solution of NaH$_2$PO$_4$ 5% (5 ml), H$_2$O (5 ml) and brine. The organic layer was dried over Na$_2$SO$_4$ and concentrated under reduced pressure. The residue was purified by flash chromatography (Biotage SP1 instrument, SNAP cartridge silica 50 g, Hex/EtOAc 9:1, 10 CV) affording the title compound (0.35 g; Yield: 83%)

$^1$H NMR (300 MHz, CDCl$_3$) δ 7.37-7.08 (m, 5H), 4.44 (t, 2H), 4.38-4.27 (m, 1H), 4.06 (t, 2H), 2.68-2.52 (m, 1H), 2.52-2.35 (m, 1H), 2.35-2.26 (m, 2H), 2.07 (s, 3H), 1.97 (m, 6H), 1.80-1.66 (m, 2H), 1.66-1.52 (m, 2H), 1.50-1.29 (m, 4H).

Example 4

Synthesis of 4-(nitrooxy)butyl 3-methyl-3-(3-methyl-1,4-dioxo-1,4-dihydronaphthalen-2-yl)butanoate (Compound 4)

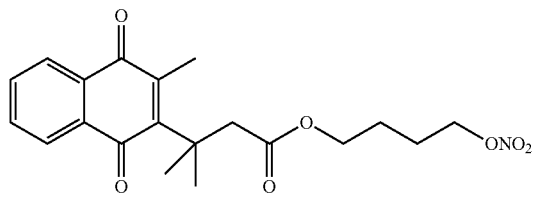

Step 1: Synthesis of 6-hydroxy-4,4,5-trimethyl-3,4-dihydro-2H-benzo[h]chromen-2-one

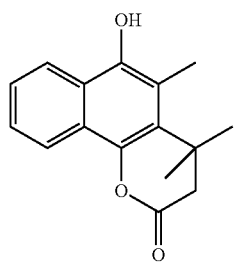

Methanesulfonic acid (30 mL) was heated at 70° C. In parallel, 2-methylnaphthalene-1,4-diol (4.75 g, 25.0 mmol) and methyl 3-methylbut-2-enoate (2.85 g, 25.0 mmol, 1 eq) were added quickly and the reaction was heated for 2 h at this temperature. The reaction was then poured in water and, after cooling, was extracted with EtOAc (3×100 mL). The combined organic layers were washed successively with water, saturated NaHCO$_3$, water and brine, dried (Na$_2$SO$_4$), filtered and evaporated. The residue was purified flash chromatography (Biotage System, 2 SNAP Cartridge silica 100 g, eluent: n-hexane/ethyl acetate 90/10 to n-hexane/ethyl acetate 70/30 during 10 CV) affording the title compound as a pale yellowish solid (2.26 g, Yield: 35%).

$^1$H NMR (300 MHz, CDCl$_3$) δ 7.90 (d, J=8.3, 2H), 7.45 (d, J=8.0, 2H), 3.88-3.67 (m, 2H), 2.45 (s, 3H), 1.56 (s, 6H).

Step 2: Synthesis of 3-methyl-3-(3-methyl-1,4-dioxo-1,4-dihydronaphthalen-2-yl)butanoic acid

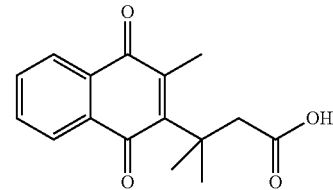 [SMILES: CC1=C(C(C)(C)CC(=O)O)C(=O)c2ccccc2C1=O]

A stirred solution of 6-hydroxy-4,4,5-trimethyl-3,4-dihydro-2H-benzo[h]chromen-2-one (1.2 g, 4.44 mmol) in 10% aqueous acetonitrile (100 mL) was added with a solution of freshly recrystallised NBS (0.8 g, 4.44 mmol, 1 eq) in acetonitrile (20 mL). The reaction was stirred for 1 h and then diluted with water (100 mL) and extracted with Et$_2$O (3×100 mL). The combined organic layers were washed with water and brine, dried (Na$_2$SO$_4$), filtered and evaporated. The residue was purified flash chromatography (Biotage System, SNAP Cartridge silica 100 g, eluent: n-hexane/ethyl acetate 70/30 to n-hexane/ethyl acetate 50/50 during 8 CV) affording the title compound as a yellow oil (0.86 g, Yield: 68%).

$^1$H NMR (300 MHz, CDCl$_3$) δ 12.11 (m, 1H), 8.06-7.99 (m, 1H), 7.87-7.78 (m, 1H), 7.70-7.58 (m, 2H), 3.02 (s, 2H), 2.14 (s, 3H), 1.44 (s, 6H).

Step 3: 4-(nitrooxy)butyl 3-methyl-3-(3-methyl-1,4-dioxo-1,4-dihydronaphthalen-2-yl)butanoate (Compound 4)

A solution of 4-hydroxybutyl nitrate (synthesized in Example 1, steps 1, 2 and 3) (150 mg, 1.11 mmol) and 3-methyl-3-(3-methyl-1,4-dioxo-1,4-dihydronaphthalen-2-yl)butanoic acid (303 mg, 1.11 mmol, 1 eq) in dry CH$_2$Cl$_2$ cooled to 0° C. was added with EDC (234 mg, 1.22 mmol, 1.1 eq) and a catalytic amount of DMAP. The reaction was stirred for 6 h at 0° C. and then washed with water, HCl 0.1 M, water and brine, dried (Na$_2$SO$_4$), filtered and evaporated. The residue was purified flash chromatography (Biotage System, SNAP Cartridge silica 100 g, eluent: n-hexane/ethyl acetate 80/20 to n-hexane/ethyl acetate 70/30 during 8 CV) affording the title compound as a yellow oil (268 mg, yield: 62%).

$^1$H NMR (300 MHz, CDCl$_3$) δ 8.02 (dd, J=6.1, 2.9, 1H), 7.89-7.80 (m, 1H), 7.70-7.58 (m, 2H), 4.36 (t, J=6.3, 2H), 3.94 (t, J=6.2, 2H), 3.10 (s, 2H), 2.32 (s, 3H), 1.67 (dt, J=10.8, 6.1, 2H), 1.65-1.45 (m, 14H).

Example 5

Synthesis of 6-(nitrooxy)hexyl 4-(4-fluorophenyl)-4-(2,4,5-trimethyl-3,6-dioxocyclohexa-1,4-dienyl)butanoate (Compound 5)

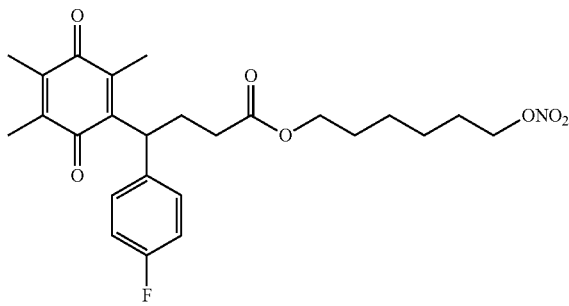

Step 1: Synthesis of 4-(2,5-dihydroxy-3,4,6-trimethylphenyl)-4-(4-fluorophenyl)butanoic acid

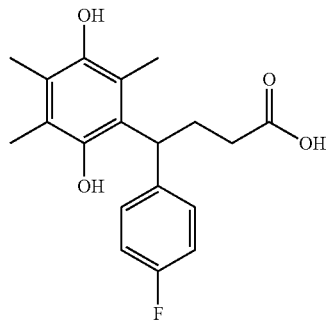 [SMILES: Cc1c(C)c(O)c(C(CCC(=O)O)c2ccc(F)cc2)c(C)c1O]

The reaction was performed according to conditions described by Mitsuru et al., J. Med. Chem. Soc., 1989, 32, 2214-2221.

Boron trifluoride etherate (0.21 ml; 1.65 mmol) was added dropwise to a mixture of trimethylhydroquinone (0.50 g; 3.30 mmol) and γ-(4-fluorophenyl)-γ-butyrolactone (0.59 g; 3.30 mmol) in toluene (10 ml) at 60° C. during 10 minutes. The mixture was stirred for further 2 hours and then the solvent was evaporated under reduced pressure. The residue was purified by flash chromatography (Biotage system, SNAP Cartridge silica 50 g, EtOAc in n-hexane from 9% to 60% in 10 CV) affording the title compound (0.48 g; Yield: 43%) as an orange solid.

Step 2: Synthesis of 4-(4-fluorophenyl)-4-(2,4,5-trimethyl-3,6-dioxocyclohexa-1,4-dien-1-yl)butanoic acid

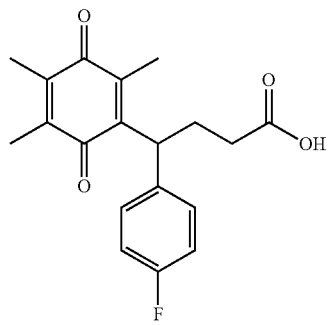 [SMILES: CC1=C(C)C(=O)C(C(CCC(=O)O)c2ccc(F)cc2)=C(C)C1=O]

To a solution of 4-(2,5-dihydroxy-3,4,6-trimethylphenyl)-4-(4-fluorophenyl)butanoic acid (0.48 g; 1.44 mmol) in $CH_3CN:H_2O$ 1:1 (40 ml), ammonium cerium nitrate (2.04 g; 3.60 mmol) was added. The mixture was stirred 3 hours at room temperature then was poured into $H_2O$ (30 ml). $Et_2O$ (20 ml) was added, the two phases were separated and the organic layer was extracted with $Et_2O$ (2×20 ml). The combined organic layers were washed with brine, dried on $Na_2SO_4$ and concentrated affording 430 mg of the title compound without any further purification.

$^1H$ NMR (300 MHz, $CDCl_3$) δ 7.32-7.19 (m, 3H), 6.97 (m, 2H), 4.29 (t, J=7.6, 1H), 2.70-2.25 (m, 4H), 2.10 (s, 3H), 2.03-1.89 (m, 6H).

Step 3: 6-(nitrooxy)hexyl 4-(4-fluorophenyl)-4-(2,4,5-trimethyl-3,6-dioxocyclohexa-1,4-dienyl)butanoate (Compound 5)

To a solution of 4-(4-fluorophenyl)-4-(2,4,5-trimethyl-3,6-dioxocyclohexa-1,4-dien-1-yl)butanoic acid (0.22 g; 0.66 mmol) and 6-Nitrooxy-hexan-1-ol (synthesised in Example 2, step 1) (0.12 mg; 0.66 mmol) in $CH_2Cl_2$ (5 ml), 1-Ethyl-3-(3-dimethylaminopropyl)carbodiimide (EDC) (0.19 g; 0.98 mmol) and DMAP cat. were added. The solution was stirred 30 minutes at 0° C. and 4 hours at room temperature then washed with a solution of $NaH_2PO_4$ 5% (5 ml), $H_2O$ (5 ml) and brine. The organic layer was dried over $Na_2SO_4$ and concentrated under reduced pressure. The residue was purified by flash chromatography (Biotage SP1 instrument, SNAP cartridge silica 50 g, Hex/EtOAc 9:1, 10 CV) affording the title compound (0.18 g; Yield: 58%).

$^1H$ NMR (300 MHz, $CDCl_3$) δ 7.36-7.17 (m, 3H), 7.05-6.88 (m, 2H), 4.44 (t, 2H), 4.28 (t, 1H), 4.06 (t, 2H), 2.67-2.33 (m, 2H), 2.33-2.22 (m, 2H), 2.11 (s, 3H), 2.00 (s, 3H), 1.95 (s, 3H), 1.80-1.55 (m, 4H), 1.49-1.30 (m, 4H).

Example 6

Synthesis of 4-(nitrooxy)butyl 4-phenyl-4-(2,4,5-trimethyl-3,6-dioxocyclohexa-1,4-dienyl)butanoate (Compound 6)

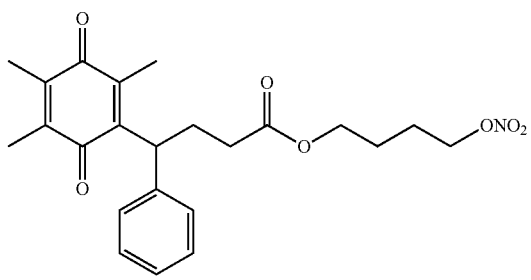

Step 1: Synthesis of 4-chlorobutyl 4-nitrobenzoate

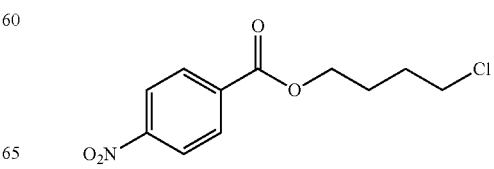

To a solution of 4-Chlorobutanol (1.09 g; 10.04 mmol) and TEA (1.7 ml; 12.05 mmol) in CH₂Cl₂ (25 ml) cooled at 0° C., 4-Nitrobenzoyl chloride (2.23 g; 12.05 mmol) was added portionwise. The mixture was stirred 2 hours at room temperature then was washed with NaH2PO4 (25 ml), H₂O and brine. The residue was purified by flash chromatography (Biotage SP1 instrument, SNAP cartridge silica 100 g, n-Hexane/EtOAc 9:1, 10 CV) affording the title compound (2.48 g; Yield: 96%)

¹H NMR (300 MHz, CDCl₃) δ 8.38-8.25 (m, 2H), 8.25-8.14 (m, 2H), 4.55-4.33 (m, 2H), 3.73-3.53 (m, 2H), 2.13-1.85 (m, 4H).

Step 2: Synthesis of 4-(nitrooxy)butyl 4-nitrobenzoate

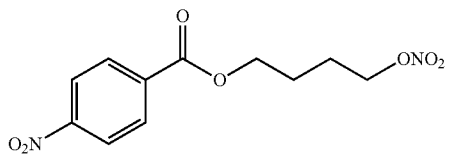

To a solution of 4-chlorobutyl 4-nitrobenzoate (2.48 g; 9.62 mmol) in CH₃CN (40 ml), NaI (5.77 g, 38.30 mmol) was added. The mixture was heated in a microwave apparatus (40 minutes; 120° C.) then the salts were filtered off and the solvent evaporated under reduced pressure. EtOAc (50 ml) was added and the solution was washed with a solution of Na₂S₂O₅ 5% (50 ml), H₂O and brine. The organic layer was dried on Na₂SO₄ and concentrated under reduced pressure. The residue was dissolved in CH₃CN (40 ml) and AgNO3 (1.97 g; 11.54 mmol) was added. The mixture was heated at the mw for 15 minutes at 120° C. then the salts were filtered off and the solvent evaporated under reduced pressure. EtOAc (30 ml) was added, the precipitate was removed again by filtration and the solvent was evaporated. This procedure was repeated three times then the organic layer was washed with brine, dried over Na₂SO₄ and concentrated under reduced pressure. The residue was purified by flash chromatography (Biotage SP1 instrument, SNAP cartridge silica 100 g, EtOAc in n-hexane from 5% to 40% in 10 CV) affording the title compound (2.50 g; Yield: 93%) as a clear oil.

Step 3: Synthesis of 4-hydroxybutyl nitrate

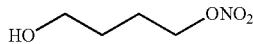

To a solution of 4-(nitrooxy)butyl 4-nitrobenzoate (2.5 g; 8.76 mmol) in THF (30 ml) cooled at 0° C., NaOH 2M (8.7 ml; 17.53 mmol) was added dropwise. The solution was stirred 4 hours at room temperature then was diluted with NaHCO3 sutured solution (20 ml) and extracted with CH₂CL₂ (3×30 ml). The combined organic layers were dried over Na₂SO₄ and concentrated under reduced pressure. The residue was purified by flash chromatography (Biotage SP1 instrument, SNAP cartridge silica 50 g, EtOAc in n-hexane from 10% to 100% in 10 CV) affording the title compound (1.0 g; Yield: 85%).

¹H NMR (300 MHz, CDCl₃) δ 4.50 (td, J=6.5, 2H), 3.70 (t, J=6.2, 2H), 1.95-1.76 (m, 2H), 1.76-1.59 (m, 2H).

Step 4: Synthesis of 4-(nitrooxy)butyl 4-phenyl-4-(2,4,5-trimethyl-3,6-dioxocyclohexa-1,4-dienyl)butanoate (Compound 6)

To a solution of 4-phenyl-4-(2,4,5-trimethyl-3,6-dioxocyclohexa-1,4-dien-1-yl)butanoic acid (synthesized in Example 3, steps 1 and 2) (0.27 g; 0.86 mmol) and 4-hydroxybutyl nitrate (0.15 mg; 0.86 mmol) in CH₂Cl₂ (4 ml), 1-Ethyl-3-(3-dimethylaminopropyl)carbodiimide (EDC) (0.25 g; 1.30 mmol) and DMAP cat. were added. The solution was stirred 30 minutes at 0° C. and 4 hours at room temperature then washed with a solution of NaH₂PO₄ 5% (5 ml), H₂0 (5 ml) and brine. The organic layer was dried over Na₂SO₄ and concentrated under reduced pressure. The residue was purified by flash chromatography (Biotage SP1 instrument, SNAP cartridge silica 50 g, Hex/EtOAc 9:1, 10 CV) affording the title compound (0.23 g; Yield: 62%) as an orange oil.

¹H NMR (300 MHz, CDCl₃) δ 7.38-7.11 (m, 5H), 4.47 (m, 2H), 4.34 (t, J=7.7, 1H), 4.09 (t, J=6.0, 2H), 2.73-2.52 (m, 1H), 2.52-2.23 (m, 3H), 2.07 (s, 3H), 1.97 (m, 6H), 1.89-1.65 (m, 4H).

Example 7

Synthesis of 4-(nitrooxy)butyl 4-(4-fluorophenyl)-4-(2,4,5-trimethyl-3,6-dioxocyclohexa-1,4-dienyl)butanoate (Compound 7)

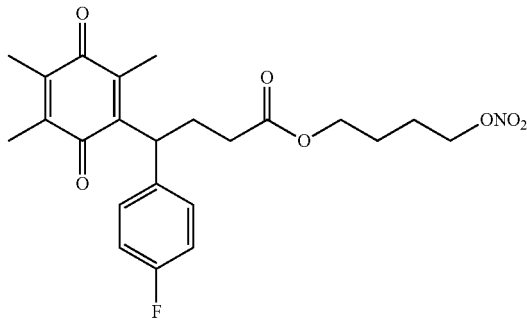

To a solution of 4-(4-fluorophenyl)-4-(2,4,5-trimethyl-3,6-dioxocyclohexa-1,4-dien-1-yl)butanoic acid (synthesized in Example 5, steps 1 and 2) (0.19 g; 0.57 mmol) and 4-hydroxybutyl nitrate (synthesized in Example 6, steps 1, 2 and 3) (0.10 mg; 0.57 mmol) in CH₂Cl₂ (4 ml), 1-Ethyl-3-(3-dimethylaminopropyl)carbodiimide (EDC) (0.16 g; 0.86 mmol) and DMAP cat. were added. The solution was stirred 30 minutes at 0° C. and 4 hours at room temperature then washed with a solution of NaH₂PO₄ 5% (5 ml), H₂O (5 ml) and brine. The organic layer was dried over Na₂SO₄ and concentrated under reduced pressure. The residue was purified by flash chromatography (Biotage SP1 instrument, SNAP cartridge silica 50 g, n-Hexane/EtOAc 9:1, 10 CV) affording the title compound (0.15 g; Yield: 59%) as an orange oil.

¹H NMR (300 MHz, CDCl₃) δ 7.35-7.15 (m, 2H), 7.06-6.87 (m, 2H), 4.47 (m, 2H), 4.28 (t, J=7.7, 1H), 4.09 (t, J=6.0, 2H), 2.68-2.22 (m, 4H), 2.08 (s, 3H), 1.97 (m, 6H), 1.86-1.65 (m, 4H).

Example 8

Synthesis of (5S,6R)-5,6-bis(nitrooxy)heptyl 3-methyl-3-(2,4,5-trimethyl-3,6-dioxocyclohexa-1,4-dienyl)butanoate ((5S,6R)-isomer of Compound 8)

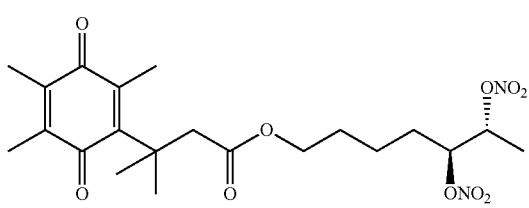

Step 1: Synthesis of hex-5-enyl 4-nitrobenzoate

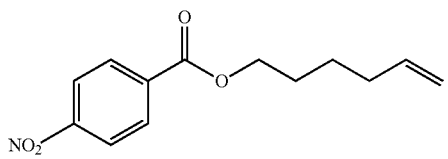 [SMILES: C=CCCCCOC(=O)c1ccc([N+](=O)[O-])cc1]

At 0° C., a solution of 5-hexen-1-ol (19.4 mL; 161.54 mmol) in dichloromethane (513 mL), was added with p-nitrobenzoyl chloride (35.97 g, 193.85 mmol) followed by a solution of triethylamine (27.0 mL, 193.85 mmol) in dichloromethane (150 mL) dropwise. The mixture was stirred at ambient temperature for 21 hours, then washed with water, 1M aqueous HCl, brine. The organic layer was dried ($Na_2SO_4$) and the solvent removed under reduced pressure. The residue was purified by flash chromatography (Biotage System, two SNAP Cartridge silica 340 g, eluent: n-hexane/ethyl acetate 90/10 to n-hexane/ethyl acetate 50/50 during 12 CV) to give the title compound as a yellow oil (40.00 g, 99%).

$^1$H NMR (300 MHz, $CDCl_3$) δ 8.30 (dt, J=9.0, 3.0 Hz, 2H), 8.22 (dt, J=9.0, 3.0 Hz, 2H), 5.83 (1H, ddt, J=16.9, 10.2, 6.7 Hz), 4.95-5.11 (2H, m), 4.39 (2H, t, J=6.6 Hz), 2.15 (2H, m), 1.84 (2H, m) 1.50-1.66 (2H, m).

Step 2: Synthesis of (5S)-5,6-dihydroxyhexyl 4-nitrobenzoate

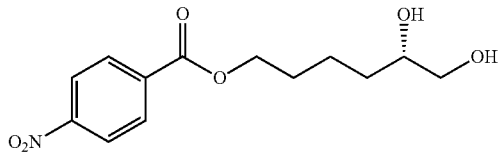 [SMILES: O=C(OCCCC[C@H](O)CO)c1ccc([N+](=O)[O-])cc1]

To a vigorously stirred solution of commercially available "AD mix α" (112.5 g) in 1:1 water/t-butanol (822 mL), at 0° C., hex-5-enyl 4-nitrobenzoate was added (20.00 g, 80.23 mmol). The mixture was stirred vigorously at 4° C. (cold room) for 21 hours. The mixture was cooled to 0° C. and ethyl acetate (450 mL) was added, followed by slow portionwise addition of sodium metabisulfite (33.1 g). The mixture was stirred at 0° C. for 30 minutes, then at ambient temperature for 1 hour. The organic phase was separated and the aqueous extracted with ethyl acetate. The combined organic extracts were washed with brine, dried ($Na_2SO_4$) and the solvent removed under reduced pressure. Purification by filtration over a short pad of silica gel, eluting with ethyl acetate, gave the title compound as an off-white solid (21.90 g, 96%).

$^1$H NMR (300 MHz, $CDCl_3$) δ 8.30 (dt, J=9.0, 2.0 Hz, 2H), 8.21 (dt, J=9.0, 2.0 Hz, 2H), 4.39 (t, J=6.6 Hz, 2H), 3.80-3.62 (2H, m), 3.47 (1H, m), 2.59 (bs, 1H), 2.42 (bs, 1H), 1.90-1.75 (2H, m), 1.73-1.45 (4H, m).

Step 3: Synthesis of (5S)-6-triphenylmethyloxy-5-hydroxyhexyl 4-nitrobenzoate

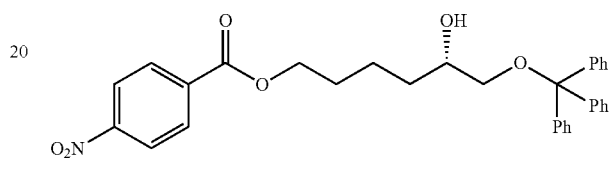

A solution of (5S)-5,6-dihydroxyhexyl 4-nitrobenzoate (13.46 g, 47.53 mmol) in anhydrous N,N-dimethylformamide (123 mL), under $N_2$, was added with triphenylchloromethane (14.57 g, 52.28 mmol), followed by triethylamine (7.29 mL, 52.28 mmol) and 4-dimethylaminopyridine (581 mg, 4.75 mmol). The resulting solution was stirred at ambient temperature for 23 hours. The mixture was poured into water and extracted with diethyl ether (×3). The combined organic extracts were washed with saturated aqueous $NH_4Cl$ and water, then dried ($Na_2SO_4$) and the solvent removed under reduced pressure. Purification by flash chromatography, eluting with 20% ethyl acetate/hexane to 50% ethyl acetate/n-hexane gave the title compound as pale yellow oil (20.90 g, 84%).

$^1$H NMR (300 MHz, $CDCl_3$) δ 8.28 (d, J=8.8 Hz, 2H), 8.20 (d, J=8.8 Hz, 2H), 7.49-7.42 (m, 6H), 7.36-7.23 (m, 9H), 4.36 (t, J=6.5 Hz, 2H), 3.82 (dp, J=10.9, 3.1 Hz, 1H), 3.21 (dd, J=9.3, 3.3 Hz, 1H), 3.07 (dd, J=9.2, 7.7 Hz, 1H), 2.36 (d, J=2.9 Hz, 1H), 1.86-1.72 (m, 2H), 1.56-1.38 (m, 4H).

Step 4: Synthesis of (5S)-6-triphenylmethyloxy-5-tert-butyldiphenylsilyloxyhexyl 4-nitrobenzoate

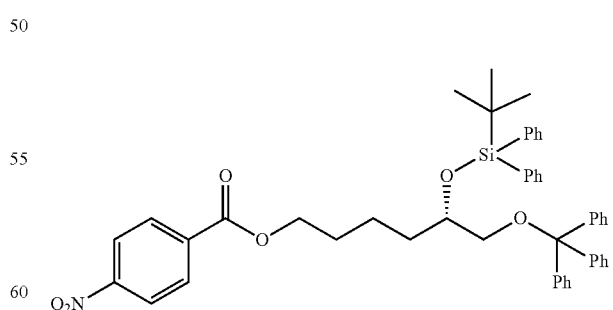

A solution of (5S)-6-triphenylmethyloxy-5-hydroxyhexyl 4-nitrobenzoate (7.10 g, 13.51 mmol) in anhydrous N,N-dimethylformamide (65 mL), under $N_2$, was added with imidazole (1.84 g, 27.02 mmol) and the solution cooled to 0° C. tert-Butyldiphenylsilyl chloride (7.03 mL, 27.02 mmol) was added and the solution stirred at 0° C. for 10 minutes, then at ambient temperature for 15 hours. The mixture was poured into water and extracted with diethyl ether. The combined organics were dried (Na₂SO₄) and the solvent removed under reduced pressure. Purification by flash chromatography, eluting with 5% ethyl acetate/n-hexane gave the title compound as off-white foam (5.29 g, 51%).

¹H NMR (300 MHz, CDCl₃) δ 8.28-8.20 (m, 2H), 8.19-8.09 (m, 2H), 7.67-7.53 (m, 4H), 7.48-7.11 (m, 21H), 4.22 (t, J=6.4 Hz, 2H), 3.97-3.87 (m, 1H), 3.15 (dd, J=9.3, 4.8 Hz, 1H), 3.03 (dd, J=9.2, 6.4 Hz, 1H), 1.78-1.44 (m, 4H), 1.27 (m, 2H), 1.02 (s, 9H).

Step 5: Synthesis of
(5S)-5-tert-butyldiphenyloxy-6-hydroxyhexyl
4-nitrobenzoate

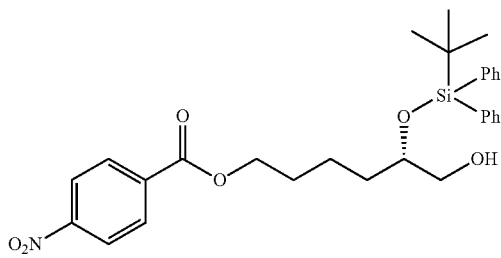 [SMILES: CC(C)(C)[Si](O[C@H](CO)CCCCOC(=O)c1ccc([N+](=O)[O-])cc1)(c1ccccc1)c1ccccc1]

A solution of (5S)-6-triphenylmethyloxy-5-tert-butyldiphenyl silyloxyhexyl-4-nitrobenzoate (4.06 g, 5.32 mmol) in dichloromethane (15 mL) was added with methanol (157 mL) and p-toluenesulfonic acid monohydrate (202 mg, 1.06 mmol). The solution was stirred at ambient temperature for 17 hours. The solvent was removed under reduced pressure and the residue dissolved in ethyl acetate and washed with saturated aqueous NaHCO₃, water, then brine. The organic layer was dried (Na₂SO₄) and the solvent removed under reduced pressure. Purification by flash chromatography (Biotage System, SNAP Cartridge silica 340 g, eluent: n-hexane/ethyl acetate 90/10 to n-hexane/ethyl acetate 70/30 during 12 CV) gave the title compound as a pale yellow oil (1.33 g, 48%).

¹H NMR (300 MHz, CDCl₃) δ 8.32-8.26 (m, 2H), 8.20-8.15 (m, 2H), 7.73-7.66 (m, 5H), 7.48-7.35 (m, 5H), 4.25 (t, J=6.5 Hz, 2H), 3.83 (dt, J=10.3, 5.3 Hz, 1H), 3.52 (ddd, J=11.4, 5.9, 3.7 Hz, 1H), 3.58 (ddd, J=11.4, 4.8, 3.1 Hz, 1H), 1.79 (bs, 1H), 1.70-1.46 (m, 4H), 1.36 (dd, J=15.0, 7.4 Hz, 2H), 1.09 (s, 9H).

Step 6: Synthesis of
(5S)-5-tert-butyldiphenylsilyloxy-6-oxo hexyl
4-nitrobenzoate

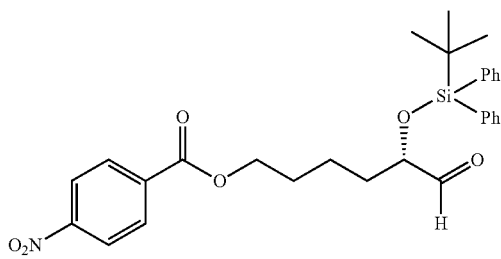 [SMILES: CC(C)(C)[Si](O[C@H](C=O)CCCCOC(=O)c1ccc([N+](=O)[O-])cc1)(c1ccccc1)c1ccccc1]

A 0.4 M solution of (5S)-5-tert-butyldiphenyloxy-6-hydroxyhexyl 4-nitrobenzoate (9.29 g, 17.81 mmol) in dichloromethane (44.5 mL) was added with silica-supported TEMPO (307 mg; 0.178 mmol), followed by a 0.5 M solution aqueous KBr (3.53 mL). The mixture was cooled to 0° C. and stirred vigorously. A 0.37 M solution of NaOCl (10-15% active CO (13.73 mL) in water (46.30 mL) was added and the mixture buffered with solid NaHCO₃. The mixture was stirred vigorously at 0° C. for 3.5 hours. The solids were removed by filtration and washed well with dichloromethane and water. The organic layer was separated and the aqueous extracted with dichloromethane. The combined organics were dried (Na₂SO₄) and the solvent removed under reduced pressure to give the title compound as crude pale yellow oil (9.09 g, 98%) for use directly without further purification.

¹H NMR (300 MHz, CDCl₃) δ 9.64 (d, J=1.4 Hz, 1H), 8.30 (dt, J=9.0, 2.0 Hz, 2H), 8.19 (dt, J=9.0, 2.0 Hz, 2H), 7.75-7.60 (m, 4H), 7.55-7.35 (m, 6H), 4.30 (t, J=6.4 Hz, 2H), 4.09 (td, J=5.6, 1.4 Hz, 1H), 1.90-1.35 (m, 6H), 1.12 (9H, s).

Step 7: Synthesis of (5S,6R)-6-hydroxy-5-terbutyldiphenyl silyloxyheptyl 4-nitrobenzoate and (5S,6S)-6-hydroxy-5-terbutyldiphenylsilyloxyheptyl
4-nitrobenzoate

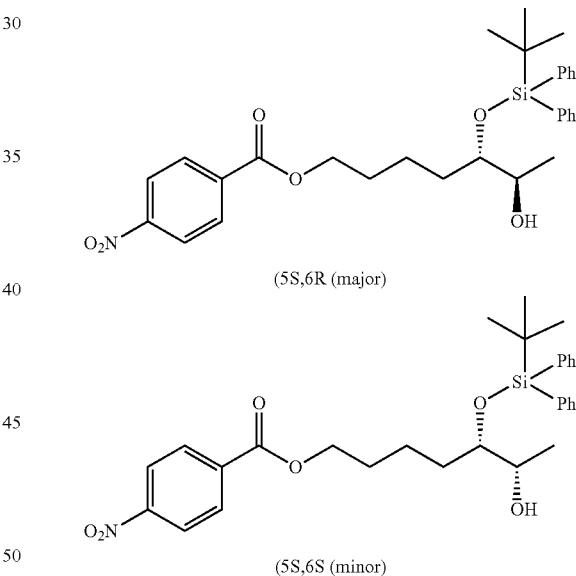

A 250 mL schlenk flask (dried and flushed with N₂) was added with (1R,2S)-(+)-(dibutylamino)-1-phenyl-1-propanol (3.28 g, 12.45 mmol, 1 eq) followed by a 2 M solution of dimethylzinc in toluene (37.35 mL, 74.7 mmol, 6 eq). The resulting yellow solution was cooled to 0° C. and a solution of (5S)-5-tert-butyldiphenylsilyloxy-6-oxohexyl 4-nitrobenzoate (6.47 g, 12.45 mmol) in anhydrous toluene (40 mL) was added slowly. The solution was stirred at 0° C. for 10 minutes then allowed to warm to ambient temperature and stirred for 18 hours. The solution was cooled to 0° C. and slowly quenched by addition of saturated aqueous NH₄Cl (75 mL). The mixture was allowed to warm to ambient temperature and extracted with ethyl acetate. The combined organics were dried (Na₂SO₄) and the solvent removed under reduced pressure. Purification by flash chromatography, eluting with 15% ethyl acetate/n-hexane to 25% ethyl acetate/n-hexane gave the title compound, a yellow oil (4.31 g, 65%), as an inseparable mixture of the diastereoisomers 5S,6R (major) and 5S,6S (minor).

(5S,6R)-major diastereoisomer
$^1$H NMR (300 MHz, CDCl$_3$) δ 8.29 (dt, J=9.0, 2.0 Hz, 2H). 8.16 (dt, J=9.0, 2.0 Hz, 2H), 7.75-7.65 (4H, m), 7.50-7.30 (6H, m), 4.20 (t, J=6.4 Hz, 2H), 3.83 (m, 1H), 3.72 (m, 1H), 2.09 (d, J=4.9 Hz, 1H), 1.65-1.20 (m, 6H), 1.12 (d, J=6.5 Hz, 3H), 1.09 (s, 9H).

(5S,6S)-minor diastereoisomer:
$^1$H NMR (300 MHz, CDCl$_3$) δ 8.29 (dt, J=9.0, 2.0 Hz, 2H), 8.16 (dt, J=9.0, 2.0 Hz, 2H), 7.75-7.65 (m, 4H), 7.30-7.50 (m, 6H), 4.20 (t, J=6.4 Hz, 2H), 3.71 (1H, m), 3.60 (1H, m), 2.21 (d, J=6.1 Hz, 1H), 1.65-1.20 (m, 6H), 1.16 (d, J=6.3 Hz, 3H), 1.09 (s, 9H).

Step 8: Synthesis of (5S,6R)-5,6-dihydroxyheptyl 4-nitrobenzoate

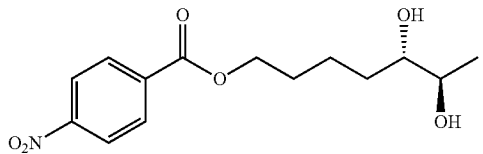 [SMILES: C[C@@H](O)[C@@H](O)CCCCOC(=O)c1ccc([N+](=O)[O-])cc1]

A solution of (5S,6R)-6-hydroxy-5-terbutyldiphenyl silyloxyheptyl 4-nitrobenzoate (805 mg, 1.50 mmol) in diethyl ether (50 mL) was added with a 3% solution of HCl in methanol, dropwise (made from addition of acetyl chloride (2.00 mL) to methanol (50 mL)). The solution was stirred at ambient temperature for 41 hours. Amberlite IRA 400 (OH) resin was added and the mixture stirred for 1 hour, with further addition of the resin until the pH=7/8. The resin was filtered off and washed with ethyl acetate, then methanol. The solvent was removed under reduced pressure and the residue partitioned between ethyl acetate and saturated aqueous NaHCO$_3$ and the aqueous extracted with ethyl acetate. The combined organics were dried (Na$_2$SO$_4$) and the solvent removed under reduced pressure. Purification by flash chromatography, eluting with 10% ethyl acetate/hexane to 90% ethyl acetate/n-hexane, gave the title compound, a pale yellow oil (189 mg, 42%), as a mixture of the diastereoisomers 5S,6R (major) and 5S,6S (minor). Diastereoisomeric excess (5S,6R)=56.4%.

The diastereoisomers were separated by preparative HPLC (conditions: column Phenomenex Gemini phenyl-hexyl 100×21.2 mm/5 m Mobile phase: A: water+0.1% Formic acid; B: methanol+0.1% formic acid.

Flow rate: 25 mL/min.

Gradient profile: time 0 min: 45% A/55% B; 5.5 min: 40% A/60% B; 5.6 min: 0% A/100% B; 7.6 min: 0% A/100% B; 7.7 min: 45% A/55% B. Detector: δ: 254 nm) to give compound H as a white solid (135 mg). Enantiomeric excess/diastereomeric excess=72.1%.

$^1$H NMR (300 MHz, CDCl$_3$) δ 8.32 (dt, J=9.0, 2.0 Hz, 2H), 8.23 (dt, J=9.0, 2.0 Hz, 2H), 4.42, (t, J=6.5 Hz, 2H), 3.84 (m, 1H), 3.66 (m, 1H), 1.42-2.0 (m, 8H), 1.19 (d, J=6.4 Hz, 3H).

Alternative Deprotection Procedure

A stirred solution of (5S,6R)-6-hydroxy-5-terbutyldiphenyl silyloxyheptyl 4-nitrobenzoate (2.96 g, 5.52 mmol) in acetonitrile (60 mL) was added at 0° C. with borontrifluoride-diethyletherate (3.5 mL, 5 eq) and the reaction was stirred at RT for 6 h. The reaction was cooled to 0° C. before quenching with a saturated solution of sodium bicarbonate. The reaction was diluted with ethyl acetate (50 mL) and the organic layer was separated, washed successively with water and brine (5 mL each), dried (Na$_2$SO$_4$), filtered and the solvent removed under reduced pressure. The residue was purified by flash chromatography (Biotage System, 2×SNAP Cartridge silica 100 g, eluent: gradient n-hexane/ethyl acetate 35/65 to n-hexane/ethyl acetate 30/70 during 7 CV) to give the title compound as a colourless oil (1.47 g, 90%) as a mixture of the diastereoisomers 5S,6R (major) and 5S,6S (minor).

The diastereoisomers were separated by preparative HPLC (conditions: column Phenomenex Gemini phenyl-hexyl 100×21.2 mm/5 m to give the major diastereoisomer as a white solid (1.09 g, 66%).

Step 9: Synthesis of (5S,6R)-5,6-bis(nitrooxy)heptyl 4-nitrobenzoate

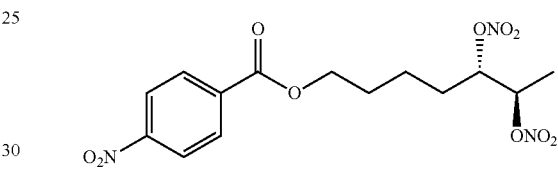

A stirred solution of (5S,6R)-5,6-dihydroxyheptyl 4-nitrobenzoate (400 mg, 1.34 mmol), tetrabutylammonium nitrate (863 mg, 2.82 mmol, 2.1 eq) and 2,6-di-tert-butyl-4-methylpyridine (580 mg, 2.82 mmol, 2.1 eq) in dry CH$_2$Cl$_2$ cooled to −78° C. was added dropwise with triflic anhydride (0.778 g, 2.75 mmol, 2.05 eq) and the reaction was stirred for 1 h at −78° C. and left to turn back to rt. The reaction was then quenched with water and the organic layer was separated, washed with water and brine, dried on sodium sulfate, filtered and evaporated. The residue was purified by flash chromatography (Biotage SP4, SNAP 100 column, EtOAc in n-hexane from 20% to 30% in 10 CV) affording the title compound as an yellow oil (406 mg, Yield: 77%).

$^1$H NMR (300 MHz, CDCl$_3$) δ 8.32 (dt, J=9.0 2.0 Hz, 2H), 8.22 (dt, J=9.0, 2.0 Hz, 2H), 5.30 (m, 1H), 4.42 (td, J=6.4 Hz, 1H), 1.95-1.55 (m, 6H), 1.43 (d, J=6.7 Hz, 3H).

Step 10: Synthesis of (1R,2S)-6-hydroxy-1-methyl-2-(nitrooxy)hexyl nitrate

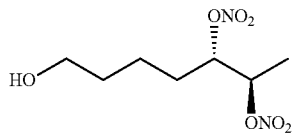

A solution of (5S,6R)-5,6-bis(nitrooxy)heptyl 4-nitrobenzoate (163 mg, 0.42 mmol) in tetrahydrofuran (1.27 mL) and ethanol (1.27 mL), was added with a 1 M aqueous NaOH solution (546 μL, 0.546 mmol). The resulting yellow solution was stirred at ambient temperature for 1.5 hours. The solvent was concentrated under reduced pressure and the aqueous residue partitioned between ethyl acetate and saturated aqueous NaHCO$_3$. The organic layer was washed with saturated aqueous NaHCO$_3$ and the aqueous back-extracted with ethyl acetate. The combined organics were dried (Na$_2$SO$_4$) and the solvent concentrated to a small volume (2 mL). The product was carefully purified by flash chromatography (Biotage System, SNAP Cartridge silica 100 g, eluent: gradient n-hexane/ethyl acetate 75/25 to n-hexane/ethyl acetate 50/50 during 8 CV) to give the separation of the two diastereoisomers and the title compound as a colourless oil (0.147 g, 90%).

An optimal separation could be obtained using a Thar Investigator SFC system using the following conditions:
Column: CHIRALPACK IB 250×10 mm (5 μm)
Cosolvent: n-Hexane/2-Propanol 1/1
Isocratic elution: CO$_2$/co-solvent 90/10
Flow 10 ml/min T column: 40° C. Injection volume: 80 μl
Detector wavelength: 210 nm
Run time: 8.5 min Cycle time: 3 min Injected amount: 14-16 mg
(Sample preparation: 800 mg of crude compound were solubilized in 4 ml of MeOH)
$^1$H NMR (300 MHz, CDCl$_3$) δ 5.25-5.34 (m, 2H), 3.70 (t, J=5.9 Hz, 2H), 1.47-1.85 (m, 7H), 1.42 (d, J=6.8 Hz, 3H).

Step 11: Synthesis of (5S,6R)-5,6-bis(nitrooxy)heptyl 3-methyl-3-(2,4,5-trimethyl-3,6-dioxocyclohexa-1,4-dienyl)butanoate (compound 8)

A stirred solution of 3-methyl-3-(2,4,5-trimethyl-3,6-dioxocyclohexa-1,4-dien-1-yl)butanoic acid (Prepared in Example 1, Step 2) (146 mg, 0.583 mmol, 1 eq) and (1R,2S)-6-hydroxy-1-methyl-2-(nitrooxy)hexyl nitrate (140 mg, 0.583 mmol) in dry CH$_2$Cl$_2$ cooled to 0° C. was added with EDC (117 mg, 0.612 mmol, 1.05 eq) and a catalytic amount of DMAP. The reaction was stirred at this temperature for 5 h and then washed with water, HCl 0.1 M, water and brine. The organic solution was dried (Na$_2$SO$_4$), filtered and evaporated. The residue was purified by flash chromatography (Biotage SP4 system, SNAP Cartridge silica 100 g, eluent: gradient n-hexane/ethyl acetate 80/20 to n-hexane/ethyl acetate 70/30 during 8 CV) to give the title compound as a yellow oil (210 mg, 76%).
$^1$H NMR (300 MHz, CDCl$_3$) δ 5.32-5.17 (m, 2H), 3.99 (t, J=6.2 Hz, 2H), 2.98 (s, 2H), 2.14 (s, 3H), 1.98-1.94 (m, 6H), 1.76-1.45 (m, 15H), 1.43 (s, 6H), 1.39 (d, J=6.7, 3H).

Example 9

Synthesis of (4-(nitrooxy)butyl 4-(4,5-dimethoxy-2-methyl-3,6-dioxocyclohexa-1,4-dienyl)-4-phenylbutanoate (Compound 9)

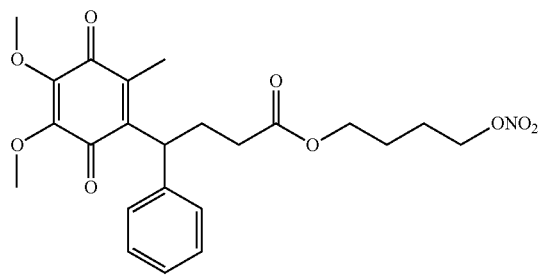

Step 1: Synthesis of 4-(2,5-dihydroxy-3,4-dimethoxy-6-methylphenyl)-4-phenylbutanoic acid

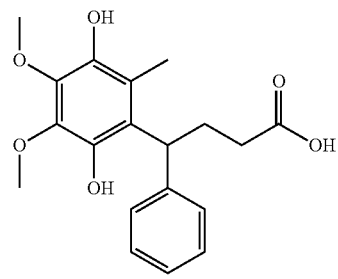 [SMILES: COc1c(O)c(C)c(C(CCC(=O)O)c2ccccc2)c(O)c1OC]

The reaction was performed according to conditions described by Mitsuru et al., J. Med. Chem. Soc., 1989, 32, 2214-2221.

Boron trifluoride etherate (0.23 ml; 1.59 mmol) was added dropwise to a mixture of 2,3-dimethoxy-5-methylbenzene-1,4-diol (1.00 g; 5.49 mmol) and γ-phenyl-γ-butyrolactone (0.89 g; 5.49 mmol) in Toluene (55 ml) at 60° C. during 10 minutes. The mixture was stirred for further 3 hours and then the solvent was evaporated under reduced pressure. The residue was purified by flash chromatography (Biotage system, SNAP Cartridge silica 100 g, EtOAc in n-hexane from 9% to 60% in 10 CV) affording the title compound (0.80 g; Yield: 42%) a pale yellow solid.
$^1$H NMR (300 MHz, CDCl$_3$) δ 7.44-7.10 (m, 5H), 5.42 (m, 2H), 4.49 (m, 1H), 3.99-3.81 (m, 6H), 2.77-2.47 (m, 2H), 2.47-2.29 (m, 2H), 2.10 (s, 3H).

Step 2: Synthesis of 4-(4,5-dimethoxy-2-methyl-3,6-dioxo cyclohexa-1,4-dien-1-yl)-4-phenylbutanoic acid

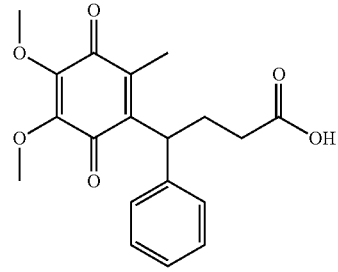 [SMILES: COC1=C(OC)C(=O)C(C(CCC(=O)O)c2ccccc2)=C(C)C1=O]

To a solution of 4-(2,5-dihydroxy-3,4-dimethoxy-6-methylphenyl)-4-phenylbutanoic acid (0.40 g; 1.15 mmol) in CH$_3$CN:H$_2$O 1:1 (40 ml), Ammonium cerium nitrate (1.63 g; 2.89 mmol) was added. The mixture was stirred 3 hours at room temperature then was poured into H$_2$O (30 ml). Et$_2$O (20 ml) was added, the two phases were separated and the organic layer was extracted with Et$_2$O (2×20 ml). The combined organic layers were washed with brine, dried on Na$_2$SO$_4$ and concentrated affording 400 mg of the title compound without any further purification.

Step 3: Synthesis of (4-(nitrooxy)butyl 4-(4,5-dimethoxy-2-methyl-3,6-dioxocyclohexa-1,4-dienyl)-4-phenylbutanoate (Compound 9)

To a solution of 4-(4,5-dimethoxy-2-methyl-3,6-dioxocyclohexa-1,4-dien-1-yl)-4-phenylbutanoic acid (0.40 g; 0.57 mmol) and 4-hydroxybutyl nitrate (synthesised in Example 6, steps 1, 2 and 3) (0.10 mg; 0.57 mmol) in $CH_2Cl_2$ (4 ml), 1-Ethyl-3-(3-dimethylaminopropyl)carbodiimide (EDC) (0.16 g; 0.86 mmol) and DMAP cat. were added. The solution was stirred 30 minutes at 0° C. and 4 hours at room temperature then washed with a solution of $NaH_2PO_4$ 5% (5 ml), $H_2O$ (5 ml) and brine. The organic layer was dried over $Na_2SO_4$ and concentrated under reduced pressure. The residue was purified by flash chromatography (Biotage SP1 instrument, SNAP cartridge silica 25 g, Hex/EtOAc 8:2, 10 CV) affording the title compound (95 mg; Yield: 36%) as a red oil.

$^1H$ NMR (300 MHz, $CDCl_3$) δ 7.38-7.15 (m, 5H), 4.49 (m, 2H), 4.35 (t, J=7.7, 1H), 4.11 (t, J=6.0, 2H), 3.98 (s, 6H), 2.74-2.52 (m, 1H), 2.52-2.25 (m, 3H), 2.09 (s, 3H), 1.89-1.66 (m, 4H).

Example 10

In Vitro Antioxidant Activity (TBARS Test)

The antioxidant properties of compound (1) (example 1), its precursors (3-methyl-3-(2,4,5-trimethyl-3,6-dioxocyclohexa-1,4-dien-1-yl)butanoic acid, described in Example 1 Step 2 (Intermediate 2) and reference antioxidant compounds were assessed after NADPH-induced lipidic peroxidation of membrane lipids in rat hepatic microsomes using the detection of 2-thiobarbituric acid reactive substances (TBARS) by visible spectroscopy.

Hepatic microsomal membranes from male Wistar rats (200-250 g) were prepared by differential centrifugation (8000 g, 20 min; 120000 g, 1 h) in a HEPES/sucrose buffer (10 mM, 250 mM, pH 7.4) and stored at −80° C. Incubation was performed at 37° C. in a Tris-HCl/KCl (100 mM/150 mM, pH 7.4) containing microsomal membranes (2 mg prot/mL), sodium ascorbate (100 μM), and DMSO solutions of the tested compounds.

Lipid peroxidation was initiated by adding $ADP\text{-}FeCl_3$ and NADPH (Method A) or 2.5 μM $FeSO_4$ (Method B) (as described by Boschi D. et al., J. Med. Chem. 2006, 49:2886-2897). Aliquots were taken from the incubation mixture at 5, 15, and 30 min and treated with trichloroacetic acid (TCA) 10% w/v.

Lipid peroxidation was assessed by spectrophotometric (543 nm) determination of the TBARS consisting mainly of malondialdehyde (MDA). TBARS concentrations (expressed in nmol/mg protein) were obtained by interpolation with a MDA standard curve. The antioxidant activity of tested compounds was evaluated as the percent inhibition of TBARS production with respect to control samples, using the values obtained after 30 min of incubation. $IC_{50}$ values were calculated by nonlinear regression analysis.

The results reported in Table 1, showed that compound (1) proved to inhibit in a concentration-dependent manner the generation of TBARS with a potency ($IC_{50}$=28 PA) that is comparable to well known antioxidant compounds as ferulic or caffeic acids, edavarone or melatonin.

TABLE 1

In vitro Antioxidant activity (TBARS test)

| Compound | Antioxidant activity IC50 μM (CL 95%) | Method |
|---|---|---|
| Compound (1) | 28 (25-31) | A |
| Intermediate 2 | 157 (79-309) | A |
| Ferulic acid | 50.5 ± 0.4[a] | B |
| Caffeic acid | 33 (32-34) | B |
| Edavarone | 17 (15-18)[b] | B |
| Melatonin | 476 (442-512)[c] | B |

Results are expressed as $IC_{50}$ of inhibition of TBARS production after 30 min incubation at 37° C.
Method A: inhibition of rat hepatic lipid peroxidation induced by $ADP\text{-}FeCl_3$ and NADPH.
Method B: inhibition of rat hepatic lipid peroxidation induced by FeSO4 and ascorbic acid
[a]tested at 1 mM concentration;
[b]Chegaev, K. et al. J. Med. Chem. 2009, 52: 574-578:
[c]Chegaev, K. et al. J. Pineal Res. 2007, 42: 371-385

Example 11

Intraocular Pressure (IOP) Lowering Activity in Hypertonic Saline-Induced IOP Increase in Rabbits The Intraocular pressure (IOP) lowering activity of compound (1) (Example 1) was assessed in an animal model of elevated IOP.

Adults male New Zealand White rabbits weighting 1.8-2.0 Kg were used in the experiments.

Animals were anesthetized using 20 mg/ml/kg of sodium pentobarbital. The increase in IOP was induced by the injection of 0.1 ml of hypertonic saline solution (5%) into the vitreous bilaterally (Krauss et al., 2011, Orihashi et al., 2005).

IOP was measured using a Tono-Pen XL prior to hypertonic saline injection (basal) and at 30, 60, 90, 120, 240 and 360 min thereafter. Vehicle (5% cremophor-EL; 0.3% DMSO; 0.2 mg/ml Benzalkonium chloride (bac) in PBS pH 6.0,) or compound of the invention were instilled as eye drops immediately after hypertonic saline injection. Eyes were randomly assigned to different treatment groups. Vehicle or compounds of the invention were directly instilled into the conjunctiva pocket at the desired doses. One drop of 0.2% oxybuprocaine hydrochloride (Novesine, Sandoz) diluted 1:1 with saline was instilled in each eye immediately before each set of pressure measurements.

Results are reported in Table 2 in which the ocular hypotensive activity of compound (1) is expressed as mean average of IOP measurements at 60 and 120 minutes following topical administration.

TABLE 2

Intraocular pressure (IOP) lowering activity in hypertonic saline-induced IOP increase in rabbits

| | IOP (mmHg) | |
|---|---|---|
| | 60 minutes | 120 minutes |
| Compound (1) | 29 ± 7.8 | 18.9 ± 4.1 |
| Vehicle | 34.9 ± 4.3 | 25.6 ± 4.6 |

Example 12

Synthesis of (S)-5,6-bis(nitrooxy)hexyl 3-methyl-3-(2,4,5-trimethyl-3,6-dioxocyclohexa-1,4-dienyl)butanoate (Compound 15; (S)-isomer of compound (10))

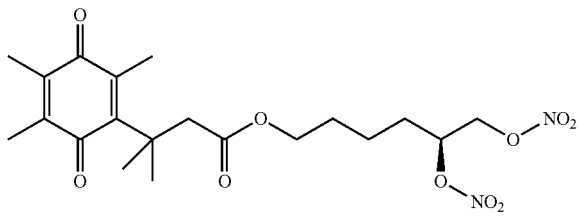 [SMILES: CC1=C(C)C(=O)C(C(C)(C)CC(=O)OCCCC[C@@H](CO[N+](=O)[O-])O[N+](=O)[O-])=C(C)C1=O]

Step 1: synthesis of (5S)-5,6-bis(nitrooxy)hexyl 4-nitrobenzoate

To a stirred solution of fuming nitric acid (7.7 mL, 91.8 mmol, 10 eq) in dichloromethane (60 mL) at −78° C., was added sulfuric acid (4 mL) and after 5 mins of stirring, a solution of (5S)-5,6-dihydroxyhexyl 4-nitrobenzoate (prepared in Example 8 Step 2) (5.2 g, 9.2 mmol) in dichloromethane (30 mL) was added and the reaction stirred at this temperature for 30 min. The crude mixture was then poured on ice and the organic layer extracted, washed with water, brine, dried over sodium sulfate, evaporated to give the title compound as pale yellow oil (6.8 g, 100%). The residue obtained was used in the next step without further purification.

1H NMR (300 MHz, CDCl3) δ 8.32 (d, J=8.9 Hz, 2H), 8.26-8.15 (m, 2H), 5.39-5.25 (m, 1H), 4.78 (dd, J=12.9, 3.1 Hz, 1H), 4.52 (dd, J=12.9, 6.4 Hz, 1H), 4.46-4.35 (m, 2H), 1.97-1.77 (m, 4H), 1.77-1.49 (m, 2H).

Step 2: Synthesis of (2S)-6-hydroxyhexane-1,2-diyl dinitrate

To a stirred solution of (5S)-5,6-bis(nitrooxy)hexyl 4-nitrobenzoate (prepared in Step 1) (6.8 g, 18.2 mmol) in a 1/1 mixture of ethanol/THF (30 mL of each) at 0° C., a 2M sodium hydroxide solution (9.1 mL, 2 eq) was added and the reaction was stirred for 2 h. The reaction was diluted with ethyl acetate and water (100 mL of each) and extracted. The organic layer was successively washed with water and brine, dried over sodium sulfate and evaporated. The oily residue was purified by column chromatography (SNAP 100, gradient system from 4/6 ethyl acetate/n-hexane to 60/40 ethyl acetate/n-hexane) to give the title compound as colorless oil (3.82 g, 93%).

1H NMR (300 MHz, CDCl3) δ 5.32 (qd, J=6.7, 3.0 Hz, 1H), 4.77 (dd, J=12.9, 3.0 Hz, 1H), 4.49 (dd, J=12.9, 6.6 Hz, 1H), 3.68 (d, J=5.5 Hz, 2H), 1.89-1.71 (m, 2H), 1.70-1.48 (m, 5H), 1.46 (s, 1H).

Step 3: Synthesis of (S)-5,6-bis(nitrooxy)hexyl 3-methyl-3-(2,4,5-trimethyl-3,6-dioxocyclohexa-1,4-dienyl)butanoate To a stirred solution of 3-methyl-3-(2,4,5-trimethyl-3,6-dioxocyclohexa-1,4-dien-1-yl)butanoic acid (201 mg; 0.80 mmol) (prepared as described in Example 1, steps 1 and 2) and (2S)-6-hydroxyhexane-1,2-diyl dinitrate (181 mg; 0.80 mmol) (prepared in Step 2) in DCM (5 ml) cooled to 0° C., EDAC (137 mg; 0.89 mmol) and a catalytic amount of DMAP were added. The reaction was stirred overnight at 0° C. The crude was then washed with water, HCl 1N, water and brine, dried and evaporated under vacuum. The crude was purified by flash chromatography [Cy/EtOAc: 0% to 20% (1CV), 20% to 40% (7CV), 40% to 60% (2CV)] affording 246 mg of the title compound (Yield: 67.1%) as a yellow oil.

1H NMR (300 MHz, acetone) δ 5.49 (qd, J=6.6, 2.6 Hz, 1H), 5.01 (dd, J=13.0, 2.6 Hz, 1H), 4.73 (dd, J=13.0, 6.3 Hz, 1H), 4.00 (t, J=6.3 Hz, 2H), 2.95 (s, 2H), 2.13 (s, 3H), 1.94 (s, J=6.3 Hz, 6H), 1.90-1.79 (m, 2H), 1.70-1.58 (m, 2H), 1.52 (dt, J=8.0, 5.7 Hz, 2H), 1.43 (s, 6H). $\alpha_D^{20}$=+2.2 (0.44% MeOH)

Example 13

Synthesis of (R)-5,6-bis(nitrooxy)hexyl 3-methyl-3-(2,4,5-trimethyl-3,6-dioxocyclohexa-1,4-dienyl)butanoate (Compound 16; (R)-isomer of compound 10)

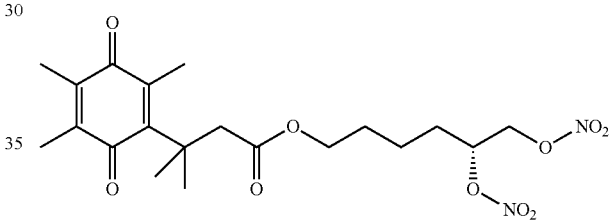

Step 1: Synthesis of (5R)-5,6-dihydroxyhexyl 4-nitrobenzoate

To a vigorously stirred solution of commercially available "AD mix β" (112.5 g) in 1:1 water/t-butanol (822 mL), at 0° C., hex-5-enyl 4-nitrobenzoate (prepared in Example 8, Step 1) was added (20.00 g, 80.23 mmol). The mixture was stirred vigorously at 4° C. (cold room) for 21 hours. The mixture was cooled to 0° C. and ethyl acetate (450 mL) was added, followed by slow portionwise addition of sodium metabisulfite (33.1 g). The mixture was stirred at 0° C. for 30 minutes, then at ambient temperature for 1 hour. The organic phase was separated and the aqueous extracted with ethyl acetate. The combined organic extracts were washed with brine, dried (Na2SO4) and the solvent removed under reduced pressure. Purification by filtration over a short pad of silica gel, eluting with ethyl acetate, gave the title compound as an off-white solid (20.5 g, 90.2%).

1H NMR (300 MHz, CDCl3) δ 8.30 (dt, J=9.0, 2.0 Hz, 2H), 8.21 (dt, J=9.0, 2.0 Hz, 2H), 4.39 (t, J=6.6 Hz, 2H), 3.80-3.62 (2H, m), 3.47 (1H, m), 2.59 (bs, 1H), 2.42 (bs, 1H), 1.90-1.75 (2H, m), 1.73-1.45 (4H, m).

Step 2: synthesis of (5R)-5,6-bis(nitrooxy)hexyl 4-nitrobenzoate

To a stirred solution of fuming nitric acid (7.7 mL, 91.8 mmol, 10 eq) in dichloromethane (60 mL) at −78° C., was added sulfuric acid (4 mL) and after 5 mins of stirring, a solution of (5R)-5,6-dihydroxyhexyl 4-nitrobenzoate (prepared in Step 1) (5.2 g, 9.2 mmol) in dichloromethane (30 mL) was added and the reaction stirred at this temperature for 30 min. The crude mixture was then poured on ice and the organic layer extracted, washed with water, brine, dried over sodium sulfate, evaporated to give the title compound as a pale yellow oil (6.8 g, 100%). The residue obtained was used in the next step without further purification.

1H NMR (300 MHz, CDCl3) δ 8.32 (d, J=8.9 Hz, 2H), 8.26-8.15 (m, 2H), 5.39-5.25 (m, 1H), 4.78 (dd, J=12.9, 3.1 Hz, 1H), 4.52 (dd, J=12.9, 6.4 Hz, 1H), 4.46-4.35 (m, 2H), 1.97-1.77 (m, 4H), 1.77-1.49 (m, 2H).

Step 3: Synthesis of (2R)-6-hydroxyhexane-1,2-diyl dinitrate

To a stirred solution of (5R)-5,6-bis(nitrooxy)hexyl 4-nitrobenzoate (prepared in Step 2) (6.8 g, 18.2 mmol) in a 1/1 mixture of ethanol/THF (30 mL of each) at 0° C., a 2M sodium hydroxide solution (9.1 mL, 2 eq) was added and the reaction was stirred for 2 h. The reaction was diluted with ethyl acetate and water (100 mL of each) and extracted. The organic layer was successively washed with water and brine, dried over sodium sulfate and evaporated. The oily residue was purified by column chromatography (SNAP 100, gradient system from 4/6 ethyl acetate/n-hexane to 60/40 ethyl acetate/n-hexane) to give the title compound as colorless oil (3.50 g, 86%).

1H NMR (300 MHz, CDCl3) δ 5.32 (qd, J=6.7, 3.0 Hz, 1H), 4.77 (dd, J=12.9, 3.0 Hz, 1H), 4.49 (dd, J=12.9, 6.6 Hz, 1H), 3.68 (d, J=5.5 Hz, 2H), 1.89-1.71 (m, 2H), 1.70-1.48 (m, 5H), 1.46 (s, 1H).

Step 4: Synthesis of (R)-5,6-bis(nitrooxy)hexyl 3-methyl-3-(2,4,5-trimethyl-3,6-dioxocyclohexa-1,4-dienyl)butanoate To a stirred solution of 3-methyl-3-(2,4,5-trimethyl-3,6-dioxocyclohexa-1,4-dien-1-yl)butanoic acid (237 mg; 0.95 mmol) (prepared as described in Example 1, steps 1 and 2) and (2R)-6-hydroxyhexane-1,2-diyl dinitrate (prepared in Step 3) (213 mg; 0.95 mmol) in DCM (5 ml) cooled to 0° C., EDAC (162 mg; 1.04 mmol) and a catalytic amount of DMAP were added. The reaction was stirred overnight at 0° C. The crude was then washed with water, HCl 1N, water and brine, dried and evaporated under vacuum. The crude was purified by flash chromatography [Cy/EtOAc: 0% to 20% (1CV), 20% to 40% (7CV), 40% to 60% (2CV)] affording 338 mg of the title compound (Yield: 78.2%) as a yellow oil.

¹H NMR (300 MHz, CDCl₃) δ 5.30-5.21 (m, 1H), 4.74 (dd, J=12.9, 3.0 Hz, 1H), 4.47 (dd, J=12.9, 6.5 Hz, 1H), 3.99 (t, J=6.3 Hz, 2H), 2.98 (s, 2H), 2.16 (d, J=7.2 Hz, 3H), 1.96 (s, 6H), 1.81-1.69 (m, 2H), 1.66-1.56 (m, 2H), 1.52-1.31 (m, 8H). $\alpha_D^{20}$=+2.3 (0.47% MeOH)

Example 14

Synthesis of (S)-5,6-bis(nitrooxy)hexyl 3-(4,5-dimethoxy-2-methyl-3,6-dioxocyclohexa-1,4-dienyl)-3-methylbutanoate (Compound 17; (S)-isomer of compound 11)

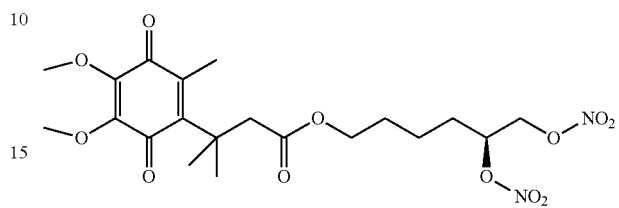

Step 1: Synthesis of 2,3-dimethoxy-5-methylbenzene-1,4-diol

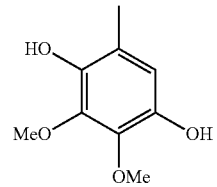

NaBH₄ (5.2 g; 137.2 mmol) was dissolved in 150 ml of water, and a solution of 2,3-dimethoxy-5-methylcyclohexa-2,5-diene-1,4-dione (Sg; 27.4 mmol) in a mixture of 75 ml of Et₂O and 38 ml of MeOH was added at room temperature with stirring. After 15 min, the mixture was placed in a separatory funnel, and the layers were allowed to separate. The ether phase was removed and the aqueous phase was extracted twice with 50 ml portions of ether. The combined organic extracts were washed with brine and dried over Na₂SO₄. Solvent removal under reduced pressure afforded the title compound (9 g; 88%) as red oil. It was used in the next step without further purification.

Step 2: Synthesis of 6-hydroxy-7,8-dimethoxy-4,4-dimethylchroman-2-one

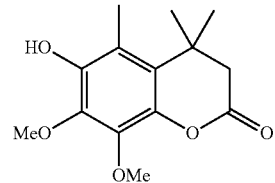

2,3-dimethoxy-5-methylbenzene-1,4-diol (obtained in Step 2) (9 g; 49 mmol), methyl 3-methylbut-2-enoate (7 ml; 58 mmol) and methanesulfonic acid (80 mL) were heated at 70° C. with stirring for 90 min. Then the mixture was poured into ice then diluted to 600 ml with water and extracted with diethyl ether (3×150 ml). The combined organic layers were washed with brine, dried over Na₂SO₄ and concentrated to dryness to afford a brown solid, which was crystallized from methanol to provide pure title compound (6.5 g; 50%) as yellow crystals.

Step 3: Synthesis of 4-nitrophenyl 3-(4,5-dimethoxy-2-methyl-3,6-dioxocyclohexa-1,4-dienyl)-3-methylbutanoate

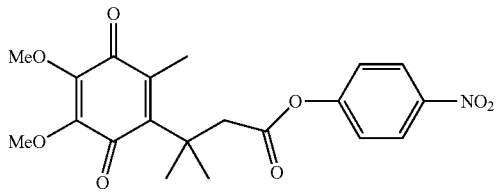 [SMILES: COC1=C(OC)C(=O)C(C(C)(C)CC(=O)Oc2ccc([N+](=O)[O-])cc2)=C(C)C1=O]

A synthetic procedure similar to the one described by Carpino et al., J. Org. Chem., 1989, 54, 3303-3310 was used, but 3-(4,5-dimethoxy-2-methyl-3,6-dioxocyclohexa-1,4-dienyl)-3-methylbutanoic acid, even if described in the paper, proved to be high unstable, so it was converted in situ into its 4-nitrophenyl ester.

Lactone obtained in Step 3 (2 g; 7.51 mmol) in DMF (15 mL) was added to a stirred solution of PDC (12.7 g; 33.7 mmol) in DMF (15 mL) at room temperature, and stirring was continued for 4 h. The mixture was diluted to 300 mL with water and extracted quickly with diethyl ether (3×150 mL). The combined ether extracts were washed with brine, dried over $Na_2SO_4$ and concentrated to about 10 mL. This solution was diluted in EtOAc (40 mL) and then p-nitrophenol (1.57 g; 11.2 mmol), DCC (2.31 g; 11.2 mmol; 1.5 eq.) and DMAP (cat) were successively added. The mixture was stirred at room temperature for 16 h, then it was concentrated to dryness. Purification by chromatography on neutral alumina (eluent: cyclohexane/AcOEt 8/2) led to the title compound (800 mg; 26%) as an orange oil.

$^1$H NMR (300 MHz, $CDCl_3$) δ 8.24 (d, 2H), 7.20 (d, 2H), 3.93 (s, 3H), 3.89 (s, 3H), 3.32 (s, 2H), 2.19 (s, 3H), 1.55 (s, 3H), 1.53 (s, 3H).

Step 4: Synthesis of (S)-5,6-bis(nitrooxy)hexyl 3-(4,5-dimethoxy-2-methyl-3,6-dioxocyclohexa-1,4-dienyl)-3-methylbutanoate

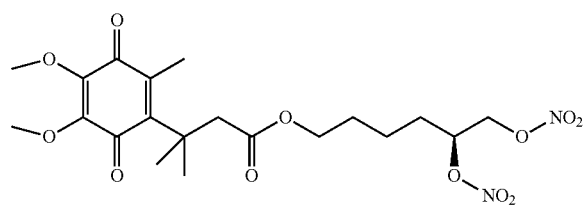 [SMILES: COC1=C(OC)C(=O)C(C(C)(C)CC(=O)OCCCC[C@@H](CO[N+](=O)[O-])O[N+](=O)[O-])=C(C)C1=O]

In a 50-ml one-necked flask, 178.0 mg (0.45 mmole) of 4-nitrophenyl dimethoxy-2-methyl-3,6-dioxocyclohexa-1,4-dienyl)-3-methylbutanoate (obtained in Step 4) and 111.0 mg (0.50 mmole) of (S)-6-hydroxyhexane-1,2-diyl dinitrate (obtained in Example 12, Step 2) were added to DCM (1.5 ml). After a 10 minutes 55.0 mg (0.45 mmole) of DMAP were added. The solution was stirred for 18 hours to room temperature. The reaction was washed with water, dried with $MgSO_4$, filtered and concentrated under reduced pressure to give red oil in a quantitative yield. The obtained red oil was purified by automatic column chromatography using silica gel Cy/DCM/MeOH (50/50/0 to 68/30/2) mixture as eluent to give 200 mg (91% yield) of the title compound as a orange oil.

MS: m/z=489 $[M+H]^+$
TLC: (Cy/DCM/MeOH 68:30:2) $R_f$=0.33
NMR ($CDCl_3$): 5.25 (m, 1H), 4.74 (dd, 1H), 4.50 (dd, 1H), 4.0 (t, 2H), 3.97 (s, 3H), 3.93 (s, 3H), 3.0 (s, 2H), 2.14 (s, 3H), 1.8-1.5 (m, 6H), 1.43 (s, 6H).

Example 15

Synthesis of (S)-5,6-bis(nitrooxy)hexyl 3-(4,5-dimethoxy-2-methyl-3,6-dioxocyclohexa-1,4-dienyl)-3-methylbutanoate (Compound 17)

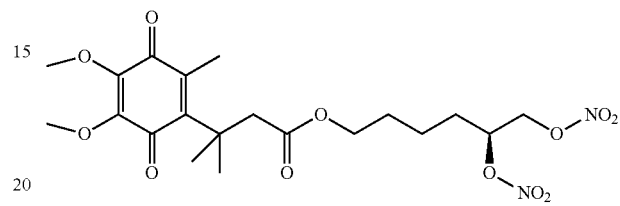

the title compound was prepared as follow:

Step 1: Synthesis of 2,5-dioxopyrrolidin-1-yl 3-(4,5-dimethoxy-3,6-dioxocyclohexa-1,4-dienyl)-3-methylbutanoate

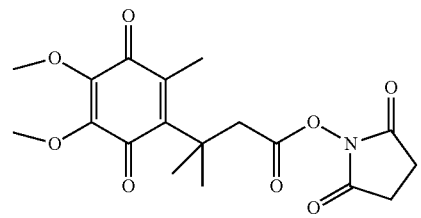 [SMILES: COC1=C(OC)C(=O)C(C(C)(C)CC(=O)ON2C(=O)CCC2=O)=C(C)C1=O]

A synthetic procedure similar to the one described by Carpino et al., J. Org. Chem., 1989, 54, 3303-3310 was used, but 3-(4,5-dimethoxy-2-methyl-3,6-dioxocyclohexa-1,4-dienyl)-3-methylbutanoic acid, even if described in the paper, proved to be high unstable, so it was converted in situ into its N-hydroxysuccinimido ester.

Lactone obtained in Example 14 Step 3 (2.5 g; 9.39 mmol) in DMF (20 mL) was added to a stirred solution of PDC (14.8 g; 39.4 mmol) in DMF (20 mL) at room temperature, and stirring was continued for 4 h. The mixture was diluted to 300 mL with water and extracted quickly with diethyl ether (3×150 mL). The combined ether extracts were washed with brine, dried over $Na_2SO_4$ and concentrated to about 10 mL. This solution was diluted in DCM (40 mL) and NHS (1.29 g; 11.2 mmol) as well as EDCl.HCl (2.16 g; 11.2 mmol) were added successively and stirring was continued for 16 h. The mixture was diluted with water and extracted with DCM. The combined organic layers were washed with brine, dried over $Na_2SO_4$ and concentrated to dryness to afford the title compound (2.74 g; 78%) as an orange oil.

$^1$H NMR (300 MHz, $CDCl_3$) δ 3.97 (s, 3H), 3.88 (s, 3H), 3.28 (s, 2H), 2.88 (s, 4H), 2.16 (s, 3H), 1.55 (s, 3H), 1.57 (s, 3H).

Step 2: Synthesis of (S)-5,6-bis(nitrooxy)hexyl 3-(4,5-dimethoxy-2-methyl-3,6-dioxocyclohexa-1,4-dienyl)-3-methylbutanoate (Compound 17)

A mixture of 40.0 mg (0.1 mmole) of 2,5-dioxopyrrolidin-1-yl 3-(4,5-dimethoxy-2-methyl-3,6-dioxocyclohexa-1,4- dienyl)-3-methylbutanoate, 28.0 mg (0.12 mmole) of (S)-6-hydroxyhexane-1,2-diyl dinitrate (prepared in Example 12, Step 2) and DMF (1 ml) were mixed together under stirring. After 10 minutes 19.0 mg (0.1 mmole) of EDC*HCl and 12.0 mg (0.1 mmole) of DMAP were added. The solution was stirred for 5 hours to 50° C. The reaction was washed with water, dried with MgSO4, filtered and concentrated under reduced pressure to give a red oil in a quantitative yield. The obtained red oil was purified by automatic column chromatography using silica gel Versaflash cartridges with Cy/DCM/MeOH (50/50/0 to 68/30/2) mixture as eluent to give 14.6 mg (31% yield) of the title compound as a orange oil.

MS: m/z=489 [M+H]$^+$

TLC: (Cy/DCM/MeOH 68:30:2) R$_f$=0.33

NMR (CDCl$_3$): 5.25 (m, 1H), 4.74 (dd, 1H), 4.50 (dd, 1H), 4.0 (t, 2H), 3.97 (s, 3H), 3.93 (s, 3H), 3.0 (s, 2H), 2.14 (s, 3H), 1.8-1.5 (m, 6H), 1.43 (s, 6H).

Example 16

Intraocular Pressure (IOP) Lowering Activity in Hypertonic Saline-Induced IOP Increase in Rabbits The present study evaluated the intraocular pressure lowering effect of single applications of two different concentrations (1% and 0.3%) of compound (1) in rabbits with experimental increase in IOP.

Adults male New Zealand White rabbits weighting 1.8-2.0 Kg were used in the experiments.

The transient increase in IOP was induced by the injection of 0.1 ml of hypertonic saline solution (5%) into the vitreous bilaterally (Krauss et al., 2011, Orihashi et al., 2005).

IOP was measured using a Tono-Pen XL prior to hypertonic saline injection (basal) and at 30, 60, 120 and 240 min thereafter. Vehicle (5% cremophor-EL; 0.3% DMSO; 0.2 mg/ml Benzalkonium chloride in PBS pH 6.0) or compound was instilled as eye drops immediately after hypertonic saline injection. Eyes were randomly assigned to different treatment groups. Vehicle and compound were directly instilled into the conjunctiva pocket at the desired doses. One drop of 0.4% oxybuprocaine hydrochloride (Novesine, Sandoz) was instilled in each eye immediately before each set of pressure measurements.

Results are reported in Table 3 and they are expressed as IOP change (at 60 and 120 minutes following topical administration) versus vehicle and versus IOP at basal before hypertonic saline injection. Single application of both doses of compound (1) resulted in a significant IOP reduction.

TABLE 3

Intraocular pressure (IOP) lowering effect of compound (1) in hypertonic saline-induced IOP increase in rabbits

| Dose | IOP change (mmHg) | |
|---|---|---|
| | 60 minutes | 120 minutes |
| 1% | −9.1 ± 3.4 | −9.5 ± 2.2 |
| 0.3% | −5.5 ± 3.1 | −5.7 ± 2.1 |

Example 17

Intraocular Pressure (IOP) Lowering Activity in Hypertonic Saline-Induced IOP Increase in Rabbits The present study evaluated the intraocular pressure lowering effect of single application of compound (15) (Example 12) and of ISMN (isosorbide-5-mononitrate) used as reference compound, in an animal model of elevated IOP.

Adults male New Zealand White rabbits weighting 1.8-2.0 Kg were used in the experiments.

Animals were anesthetized using 20 mg/ml/kg of sodium pentobarbital. The increase in IOP was induced by the injection of 0.1 ml of hypertonic saline solution (5%) into the vitreous bilaterally (Krauss et al., 2011, Orihashi et al., 2005).

IOP was measured using a Tono-Pen XL prior to hypertonic saline injection (basal) and at 30, 60, 90, 120, 240 and 360 min thereafter. Vehicle (5% cremophor-EL; 0.3% DMSO; 0.2 mg/ml Benzalkonium chloride in PBS pH 6.0,) or tested compound was instilled as eye drops immediately after hypertonic saline injection. Eyes were randomly assigned to different treatment groups. Vehicle or compounds were directly instilled into the conjunctiva pocket at the desired doses. One drop of 0.2% oxybuprocaine hydrochloride (Novesine, Sandoz) diluted 1:1 with saline was instilled in each eye immediately before each set of pressure measurements.

Results are reported in Table 4 and they are expressed as IOP change (at 30 and 60 minutes following topical administration) versus vehicle and versus IOP at basal before hypertonic saline injection.

Single application of compound (15) resulted in a significantly higher IOP reduction as compared to ISMN treated group.

TABLE 4

Intraocular pressure (IOP) lowering effect in hypertonic saline-induced IOP increase in rabbits

| Compound/dose | IOP change (mmHg) | |
|---|---|---|
| | 30 minutes | 60 minutes |
| Compound (15) (1%) | −6.5 ± 2.6 | −4.9 ± 2.4 |
| ISMN (1%) | −2.6 ± 3.5 | −0.7 ± 2.9 |

The invention claimed is:

1. A compound of formula (I)

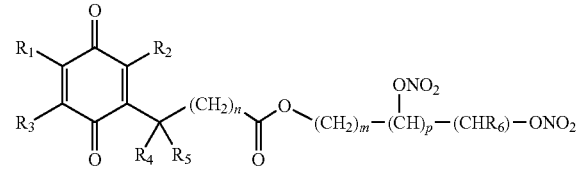

(I)

or stereoisomers thereof, wherein:

R$_1$ is selected from H, methyl, methoxy;

R$_2$ is H or methyl;

R$_3$ is selected from H, methyl, methoxy;

or R$_1$ and R$_3$ together form —CH═CH—CH═CH—;

R$_4$ and R$_5$ are methyl and n is 1, or

R$_4$ is H, R$_5$ is selected from phenyl, para-fluorophenyl, para-methoxyphenyl, para-isopropylphenyl, para-trifluoromethyl phenyl or para-methylphenyl and n is 2;

m is an integer from 1 to 10;

p is 0 or 1;

R$_6$ is H or methyl.

2. A compound of formula (I) according to claim 1 wherein
$R_2$ is methyl;
$R_4$ and $R_5$ are methyl and n is 1.

3. A compound of formula (I) according to claim 1 wherein
$R_2$ is methyl;
$R_4$ is H, $R_5$ is selected from phenyl, para-fluorophenyl, para-methoxyphenyl, para-isopropylphenyl, para-trifluoromethylphenyl or para-methylphenyl and n is 2.

4. A compound of formula (I) according to claim 2 wherein
$R_1$ and $R_3$ are methyl.

5. A compound of formula (I) according to claim 2 wherein
$R_1$ and $R_3$ are methoxy.

6. A compound of formula (I) according to claim 2 wherein $R_1$ and $R_3$ together form —CH═CH—CH═CH—.

7. A compound of formula (I) according to claim 2 wherein $R_1$ is methyl and $R_3$ is methoxy.

8. A compound of formula (I) according to claim 2 wherein $R_1$ is methoxy and $R_3$ is methyl.

9. A compound of formula (I) according to claim 4 wherein p is 0 and $R_6$ is H.

10. A compound of formula (I) according to claim 4 wherein p is 1.

11. A compound of formula (I) according to claim 3 wherein $R_1$ and $R_3$ are methyl.

12. A compound of formula (I) according to claim 3 wherein
$R_1$ and $R_3$ are methoxy.

13. A compound of formula (I) according to claim 3 wherein $R_1$ and $R_3$ together form —CH═CH—CH═CH—.

14. A compound of formula (I) according to claim 3 wherein $R_1$ is methyl and $R_3$ is methoxy.

15. A compound of formula (I) according to claim 3 wherein $R_1$ is methoxy and $R_3$ is methyl.

16. A compound of formula (I) according to claim 11 wherein p is 0 and $R_6$ is H.

17. A compound of formula (I) according to claim 11 wherein p is 1.

18. A compound of formula (I) according to claim 1 selected from:
4-(nitrooxy)butyl 3-methyl-3-(2,4,5-trimethyl-3,6-dioxocyclohexa-1,4-dienyl)butanoate (Compound 1);
6-(nitrooxy)hexyl 3-methyl-3-(2,4,5-trimethyl-3,6-dioxocyclohexa-1,4-dienyl)butanoate (Compound 2);
6-(nitrooxy)hexyl 4-phenyl-4-(2,4,5-trimethyl-3,6-dioxocyclohexa-1,4-dienyl)butanoate (Compound 3);
4-(nitrooxy)butyl 3-methyl-3-(3-methyl-1,4-dioxo-1,4-dihydro naphthalene-2-yl)butanoate (Compound 4);
6-(nitrooxy)hexyl 4-(4-fluorophenyl)-4-(2,4,5-trimethyl-3,6-dioxocyclohexa-1,4-dienyl)butanoate (Compound 5);
4-(nitrooxy)butyl 4-phenyl-4-(2,4,5-trimethyl-3,6-dioxocyclohexa-1,4-dienyl)butanoate (Compound 6);
4-(nitrooxy)butyl 4-(4-fluorophenyl)-4-(2,4,5-trimethyl-3,6-dioxocyclohexa-1,4-dienyl)butanoate (Compound 7);
(5S,6R)-5,6-bis(nitrooxy)heptyl 3-methyl-3-(2,4,5-trimethyl-3,6-dioxo cyclohexa-1,4-dienyl)butanoate (Compound 8);
4-(nitrooxy)butyl 4-(4,5-dimethoxy-2-methyl-3,6-dioxocyclohexa-1,4-dienyl)-4-phenylbutanoate (Compound 9);
5,6-bis(nitrooxy)hexyl-3-methyl 3-(2,4,5-trimethyl-3,6-dioxocyclohexa-1,4-dienyl)butanoate (Compound 10)
5,6-bis(nitrooxy)hexyl 3-(4,5-dimethoxy-2-methyl-3,6-dioxocyclohexa-1,4-dienyl)-3-methylbutanoate (Compound 11)
4-(nitrooxy)butyl 3-(4,5-dimethoxy-2-methyl-3,6-dioxocyclohexa-1,4-dienyl)-3-methylbutanoate (Compound 12)
5,6-bis(nitrooxy)hexyl 4-(4,5-dimethoxy-2-methyl-3,6-dioxocyclohexa-1,4-dienyl)-4-phenylbutanoate (Compound 13)
5,6-bis(nitrooxy)hexyl 4-phenyl-4-(2,4,5-trimethyl-3,6-dioxocyclohexa-1,4-dienyl)butanoate (Compound 14)
(S)-5,6-bis(nitrooxy)hexyl 3-methyl-3-(2,4,5-trimethyl-3,6-dioxocyclohexa-1,4-dienyl)butanoate (Compound 15)
(R)-5, 6-bis(nitrooxy)hexyl 3-methyl-3-(2, 4, 5-trimethyl-3, 6-dioxocyclohexa-1,4-dienyl)butanoate (Compound 16)
(S)-5,6-bis(nitrooxy)hexyl-3-(4,5-dimethoxy-2-methyl-3,6-dioxocyclohexa-1,4-dienyl)-3-methylbutanoate (Compound 17),
and stereoisomers thereof.

19. A method for treating hypertensive glaucoma, normotensive glaucoma, secondary glaucoma and/or ocular hypertension comprising administering to a subject in need thereof the compound of formula (I).

20. A method for treating age related macular degeneration, diabetic retinopathy, macular degeneration, inflammatory retinal disease, and/or uveitis comprising administering to a subject in need thereof the compound according to claim 1.

21. An ophthalmic composition comprising a compound of formula (I) according to claim 1 and at least an ophthalmically acceptable component and/or ophthalmically acceptable vehicle.

22. A composition comprising a compound of formula (I) according to claim 1 and one or more further active ingredients selected from alpha adrenergic agonists, beta blockers, carbonic anhydrase inhibitors, prostaglandin analogs, non-steroidal anti-inflammatory drugs, or a steroidal anti-inflammatory drugs.

23. A method for treating hypertensive glaucoma, normotensive glaucoma, secondary glaucoma and/or ocular hypertension comprising administering to a subject in need thereof of composition according to claim 22.

24. A method for treating age related macular degeneration, diabetic retinopathy, macular degeneration, inflammatory retinal disease, and/or uveitis comprising administering to a subject in need thereof the composition according to claim 21.

25. An ophthalmic composition comprising a composition according to claim 22 and at least an ophthalmically acceptable component and/or ophthalmically acceptable vehicle.

* * * * *